United States Patent [19]

Dion

[11] 4,338,821

[45] Jul. 13, 1982

[54] LIQUID CRYSTAL CELL FOR ACOUSTICAL IMAGING

[76] Inventor: Jean-Luc Dion, 3760 rue Montpellier, Trois-Rivieres Ouest, Quebec, Canada, G8Y 3P2

[21] Appl. No.: 84,087

[22] Filed: Oct. 12, 1979

[30] Foreign Application Priority Data

Oct. 13, 1978 [CA] Canada .................................. 313460

[51] Int. Cl.³ .......................... G01N 29/00; G02F 1/11
[52] U.S. Cl. ........................................ 73/603; 350/330
[58] Field of Search ................. 73/603, 604, 655, 656; 350/330, 340, 342; 367/7, 8, 10

[56] References Cited

U.S. PATENT DOCUMENTS

| | | | |
|---|---|---|---|
| 3,597,043 | 8/1971 | Dreyer | 73/655 |
| 3,707,323 | 12/1972 | Kessler et al. | 350/358 |
| 3,831,434 | 8/1974 | Greguss | 73/603 |
| 3,972,733 | 8/1976 | Kamei et al. | 350/330 |
| 3,989,354 | 11/1976 | Dubois et al. | 350/340 |
| 3,991,606 | 11/1976 | Dreyer | 73/603 |
| 4,156,558 | 5/1979 | Grumet | 350/340 |

FOREIGN PATENT DOCUMENTS

| | | |
|---|---|---|
| 914684 | 7/1949 | Fed. Rep. of Germany . |
| 2177410 | 11/1973 | France . |
| 2368108 | 5/1978 | France . |

OTHER PUBLICATIONS

J. L. Dion et al., "A New Hypothesis on Ultrasonic Interaction with a Nematic Liquid Crystal", *Applied Physics Letters*, vol. 31, No. 8, pp. 490-493, Oct. 1977.

P. Greguss, "A New Liquid Crystal Acoustical-to-Optical Display", *Acustica*, vol. 29, Heft 1, pp. 52-58, 1973.

S. Nagai et al., "Acousto-Optical Effects in Nematic Liquid Crystal", *Revue de Physique Appliquer*, vol. 12, No. 2, pp. 21-30, Jan. 1977.

J. L. Dion et al., "Physique Cristalline", *Compte Rendu Acad. Sc. Paris*, vol. 284, No. 11, pp. 219-222, Mar. 1977.

*Primary Examiner*—Stephen A. Kreitman
*Attorney, Agent, or Firm*—Schwartz, Jeffery, Schwaab, Mack, Blumenthal & Koch

[57] ABSTRACT

The invention is related to an acousto-optical liquid crystal cell and the ways of using it in acoustical holography and imaging systems. The molecules of the liquid crystal layer can be reoriented in a direction perpendicular to the direction of an ultrasonic wave propagating in the medium. The cell has multi-layered walls providing high acoustical transparency for waves incident at various angles, such that multiple reflections and parasitic effects in the liquid crystal are reduced. This results in a wide acoustic imaging field and high resolving power for details of an acoustic object. This cell makes possible the direct and real-time conversion of an acoustical hologram into a visible image representing at will the intensity on the phase variations of ultrasonic waves coming from the internal structures of a body.

12 Claims, 31 Drawing Figures

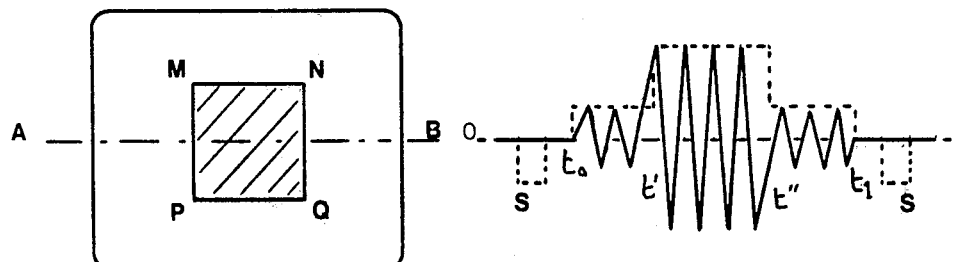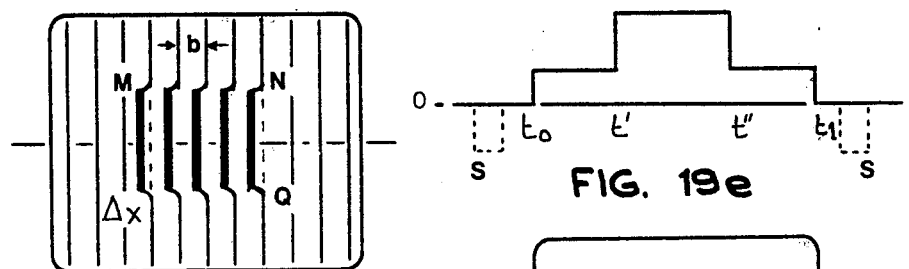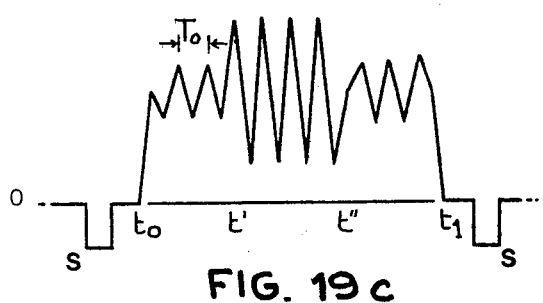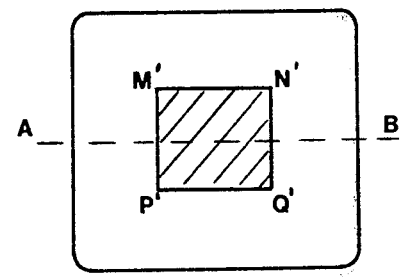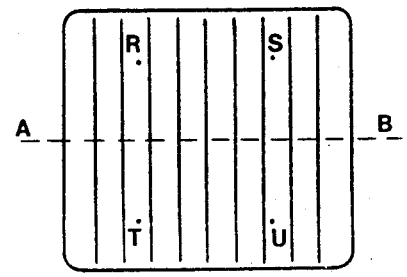
FIG. 19a
FIG. 19b
FIG. 19c
FIG. 19d
FIG. 19e
FIG. 19f
FIG. 19g

LIQUID CRYSTAL CELL FOR ACOUSTICAL IMAGING

This invention relates to the field of acoustical imaging with liquid crystal detectors.

The invention relates more particularly to the ways of assembling nematic liquid crystal acousto-optical cells with multi-layered walls, permitting direct and real-time conversion of the acoustical hologram of an object and internal structures into a visible image. With the appropriate means described herein, these cells or convertors allow improved sensitivity to ultrasonic energy, better resolving power and dynamic range, as compared with the previous art.

Acoustical imaging and holography are primarily related to the various means of obtaining visual representations of objects or bodies, particularly of their hidden structures, by detection of the acoustical energy transmitted, reflected or scattered by these structures, and converting this distribution of energy into a visible image.

Various acoustical imaging techniques are presently used, including acoustical holography, to produce visible images of bodies radiating ultrasonic energy. Ultrasonic echography is one technique currently used in medicine and non-destructive testing to obtain two dimensional views of the inner structure of bodies. For example, axial tomographies or transverse views of an object can be obtained with an ultrasonic beam of energy. Some systems have a single mechanically scanned ultrasonic transducer and are rather slow. Others have a multiplicity of transducers in one or two dimensional arrays, associated with a highly complex electronic signal processing system. Numerous articles on the subject may be found in publications such as, for example, "IEEE Transactions on Sonics and Ultrasonics", "Ultrasonics" (G.B.), "Journal of the Acoustical Society of America", "Journal of Applied Physics", etc. Various systems of this type are described in the article "Status of Research in Acoustic Imaging", by H. W. Jones, in "Acousto-Optics", vol. 90, pp. 82-100 (Soc. of Photo-Optical Instrum. Eng., 1976). Although these are real-time operating systems, their resolving power is generally quite low.

Liquid surface deformation acoustical holography is also a current technique. Its principles and realizations are particularly described in U.S. Pat. Nos. 3,879,989 and 3,765,403, by B. B. Brenden. This inventor has written articles on the subject, such as: "History and Present Status of Liquid Surface Acoustical Holography", in J. Acoust. Soc. Am., vol. 58, No. 5 (1975), p. 951-955. In this process, the image of the object is formed on the surface of a liquid by means of an acoustic lens. A second beam of acoustic coherent waves is directed on the surface where an interference pattern is formed by radiation pressure, which constitutes the acoustical hologram of the object. A powerful beam of coherent laser light is simultaneously diffracted by this pattern and processed in an appropriate optical system to give a visible image of the acoustical object. However, acoustical imaging systems based on this principle generally have low sensitivity and the images may have important defects due to coherence of ultrasound. Furthermore, the detector being a horizontal liquid surface, the possible arrangements of the system are limited and is subject to disturbing vibrations.

Various descriptions of other acoustical imaging and holography techniques may be found in several review articles, particularly: "Acoustic Imaging with Halography and Lenses", by G. Wade, IEEE Trans. Sonics Ultrasonics, vol. SU-22, No. 6 (1975), pp. 385-394; "Holography and Acoustics", by P. Greguss, in "Acoustics and Vibration Progress", edited by R. V. B. Stephens and H. G. Leventhal (Chapman and Hall, London, 1976); also "Imagerie et holographie ultrasonore", by Pierre Alais, Revue de Physique Appliquee, vol. 11, No. 5 (1976), pp. 559-580. A technique particularly described uses a Pohlmann Cell. This quadratic detector if formed by a suspension of metallic micro-discs in a thin layer of a dense liquid between flat walls, one of which at least is transparent to ultrasonic energy. An acoustic field is made visible by the re-orientation and migration of the micro-discs it produces. The sensitivity of the device is low (1 mW/cm$^2$), and its response time over 1 second. Another device of the previous art is the liquid crystal cell described by Greguss in the above mentioned article. This cell is described more precisely in another article by the same author: "A New Liquid Crystal Acoustical-to-Optical Display", in Acustica, vol. 29, No. 1 (1973). This display incorporates a nematic liquid crystal layer and has a low sensitivity: the intensity of the incident acoustic waves must be of several mW/cm$^2$ to produce a visible interaction. This device of the previous art also has a narrow acoustic object field. Furthermore acoustic mode coupling in the wall of the cell produce undesirable shear vibrations and artifacts in the images.

The object of this invention is a variety of ways to circumvent several drawbacks of the above mentioned acousto-optical detectors or convertors, and primarily the methods of making acousto-optical liquid crystal cells operating on a new interaction mode between the acoustic wave vector and the orientation of nematic liquid crystal molecules. This coupling mode produces a distortion of the liquid crystal structure accompanied by visible changes of its optical properties for acoustic intensities much lower than those required in cells of the previous art.

More exactly, the present invention relates to acousto-optical cells having an oriented liquid crystal layer enclosed between multi-layered or stratified walls, these walls presenting an acoustic impedance matched to the impedance of the adjacent propagation media, for widely varying angles of incidence, the molecules of the said liquid crystal being re-orientable in a direction substantially perpendicular to the propagation direction of the incident ultrasonic energy, each wall comprising at least two layers transparent to the said ultrasonic energy, and at least one wall being optically transparent.

The invention also relates to the various ways of using the said liquid crystal cells or convertors for acoustical imaging and holography.

Other objects and advantages of this invention will be apparent from the description that follows, the drawings and the claims.

Figure 3:
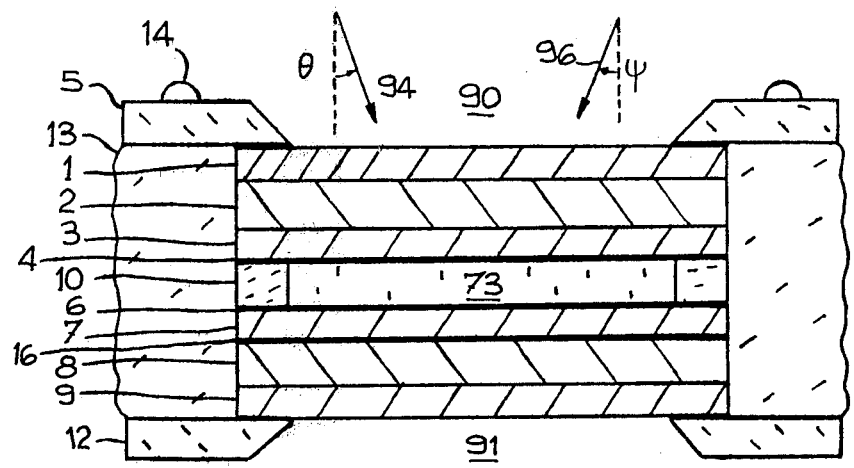

FIG. 3 presents an embodiment of the liquid crystal cell with solid stratified walls.

Figure 4:
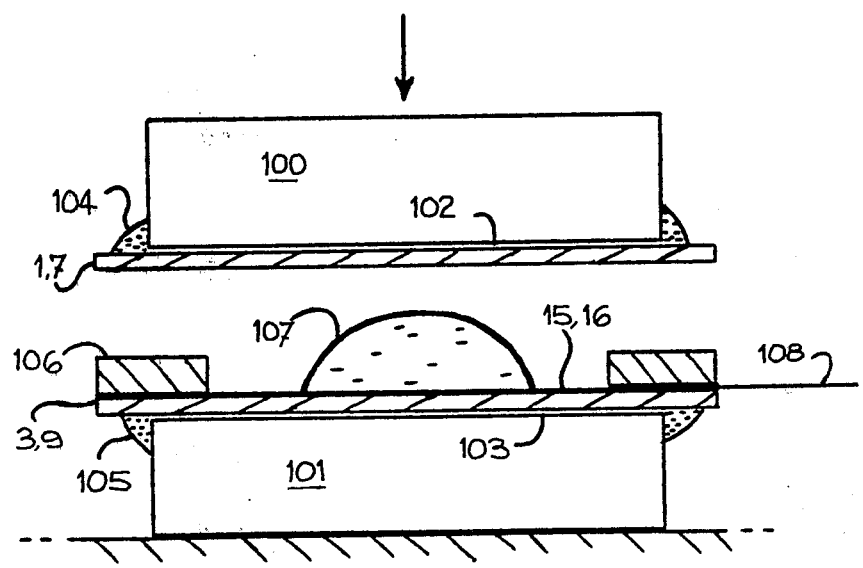

FIG. 4 illustrates a preferred way of assembling the layered walls of an acousto-optical cell.

Figure 5:
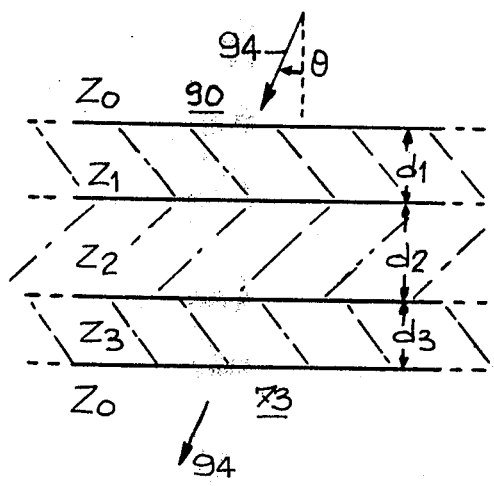

FIG. 5 shows an acoustic wave propagating in a layered medium.

Figure 6:
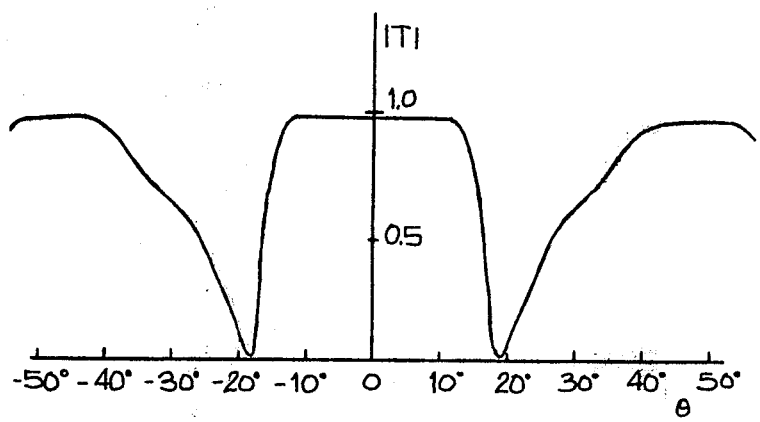

FIG. 6 shows the typical variation of acoustic pressure transmission coefficient of a layered-wall cell as a function of the angle of incidence.

Figure 7:
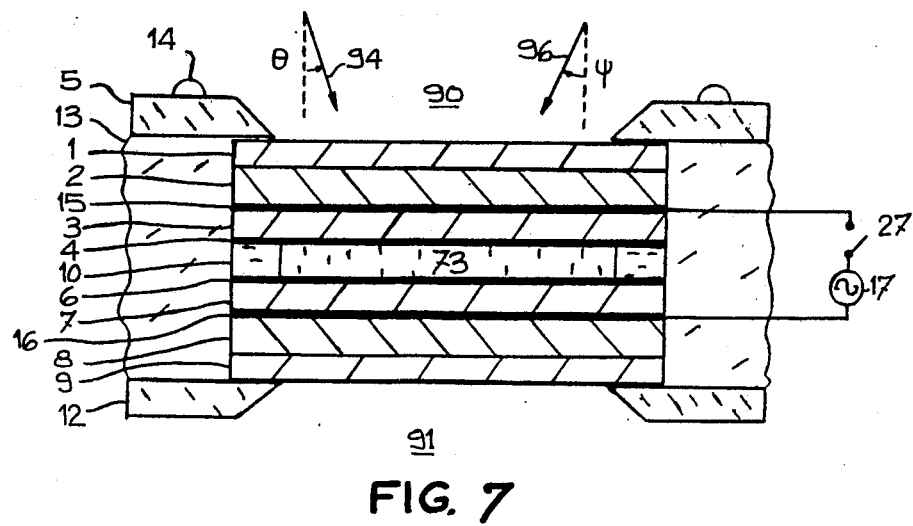

FIG. 7 presents a liquid crystal acousto-optical cell where an electric field can be produced to re-orient the liquid crystal molecules.

Figure 8:
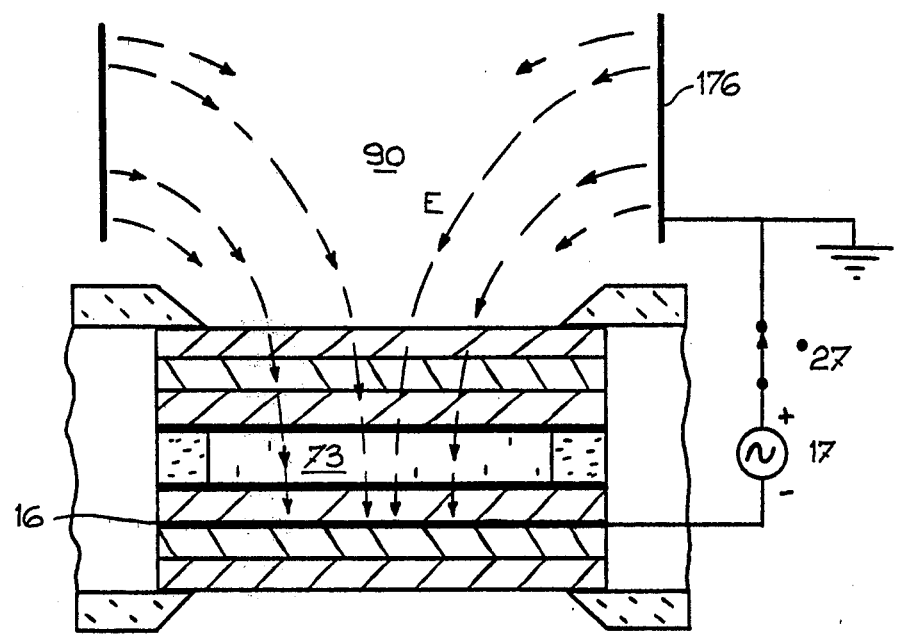

FIG. 8 shows an acousto-optical cell with a single internal electrode for the purpose of producing a re-orienting electric field.

Figure 9:
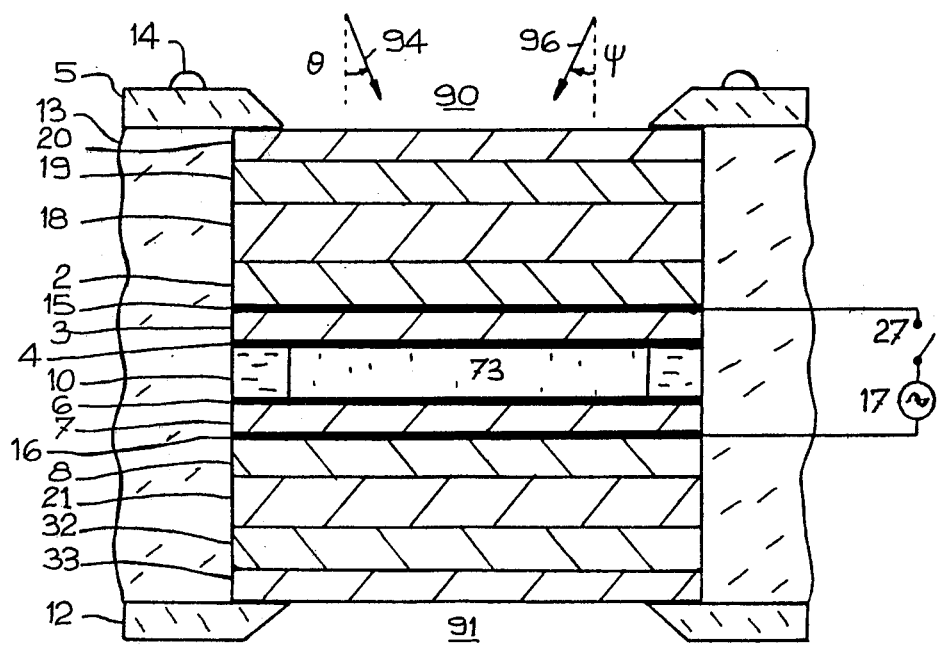

FIG. 9 illustrates an acousto-optical cell with high stiffness.

Figure 10:
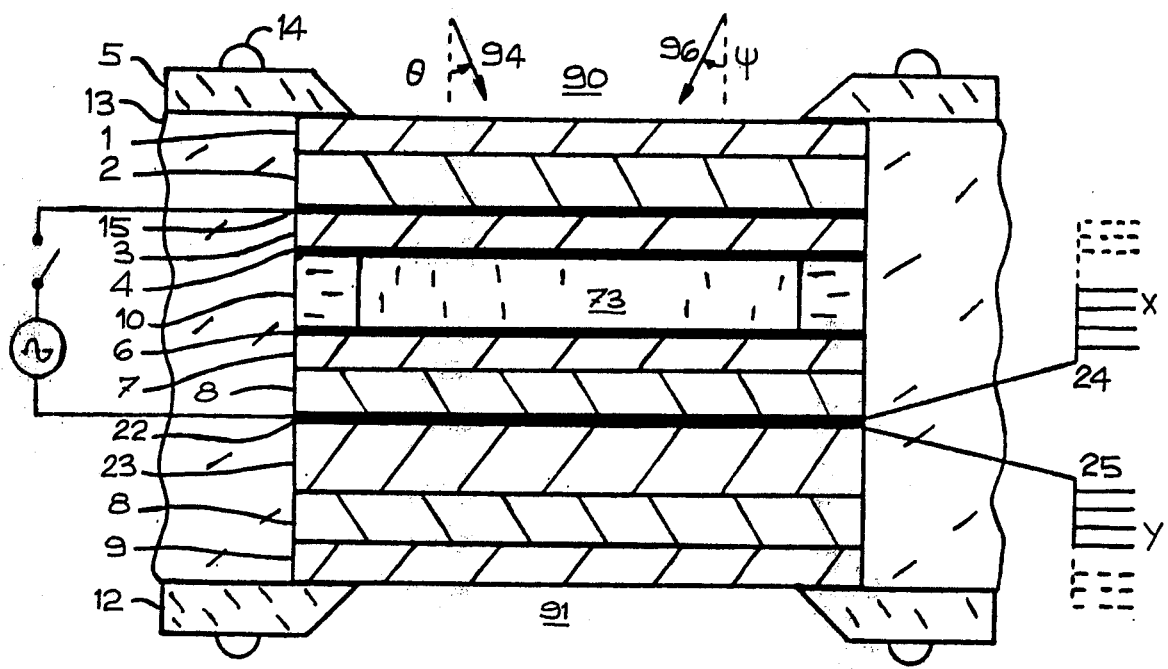

FIG. 10 is a diagram showing an acousto-optical cell incorporating a photo-detector matrix.

Figure 11:
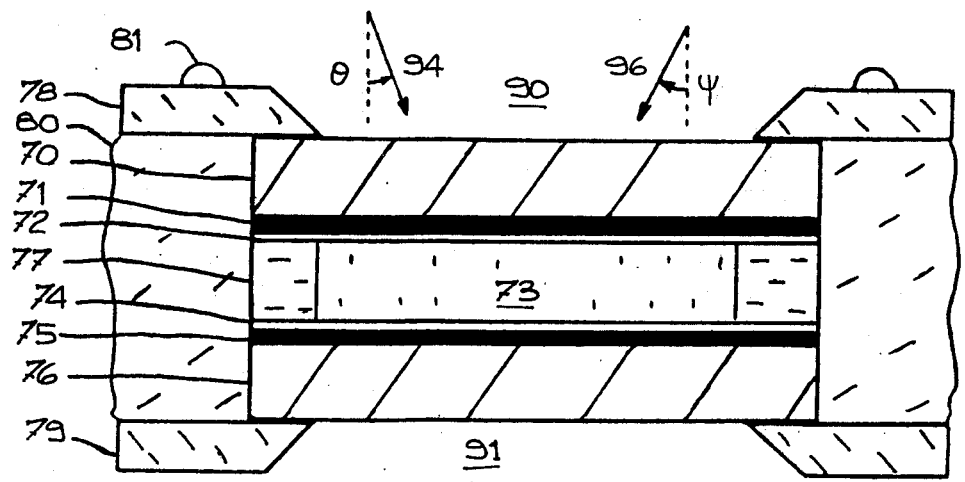
Figure 12:
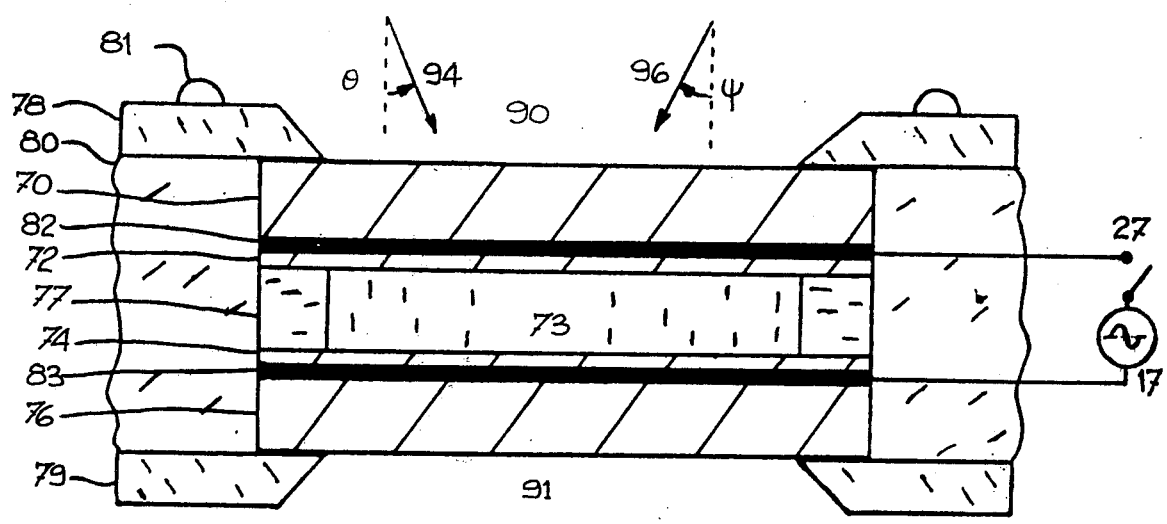

FIGS. 11 and 12 represents acousto-optical cells with walls composed of stretched polymeric films.

Figure 13:
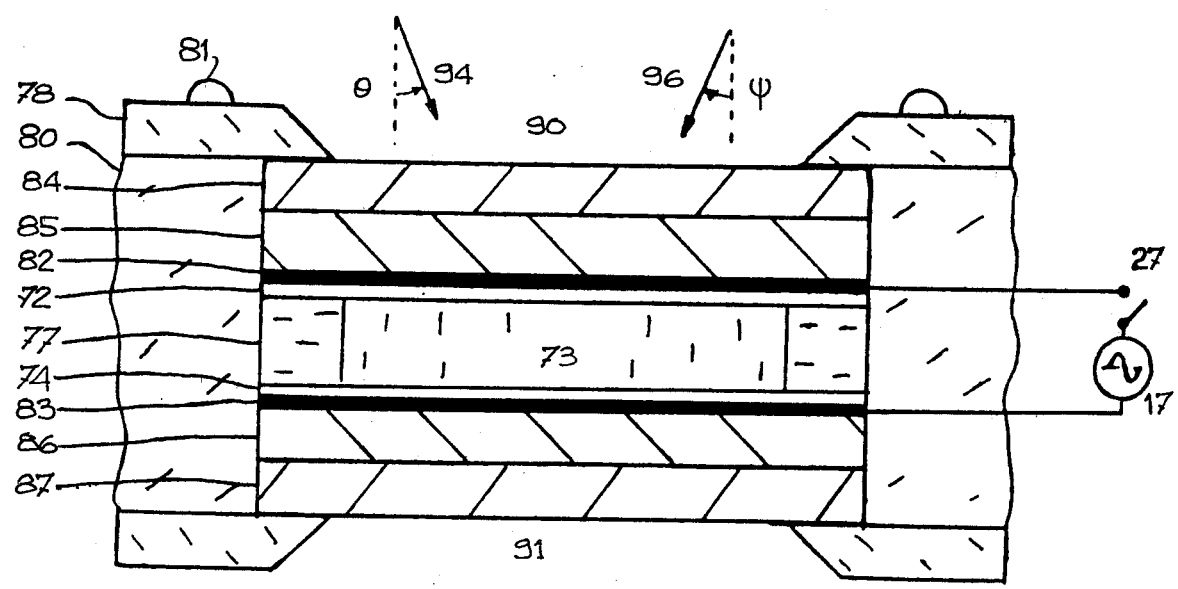

FIG. 13 shows an acousto-optical cell with stretched film walls, one of which is polarizing, the other being birefringent.

Figure 14:
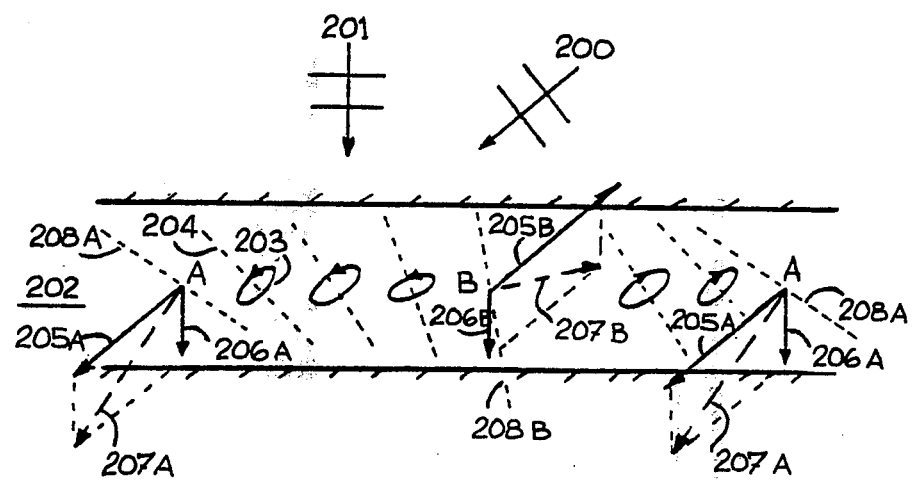

FIG. 14 illustrates the action of two coherent ultrasonic waves on the orientation of a liquid crystal layer.

Figure 15:
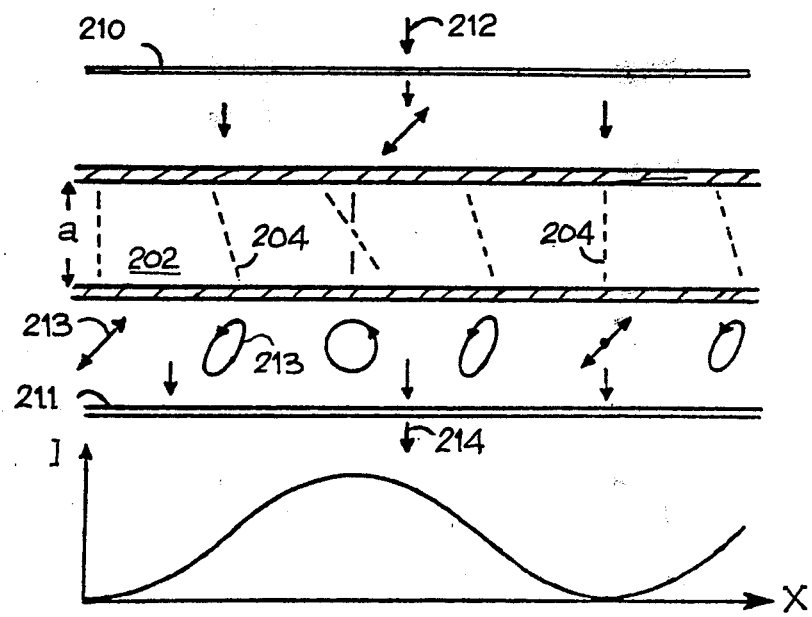

FIG. 15 shows the effect of molecular re-orientation in the liquid crystal on transmission of light through the cell.

Figure 16:
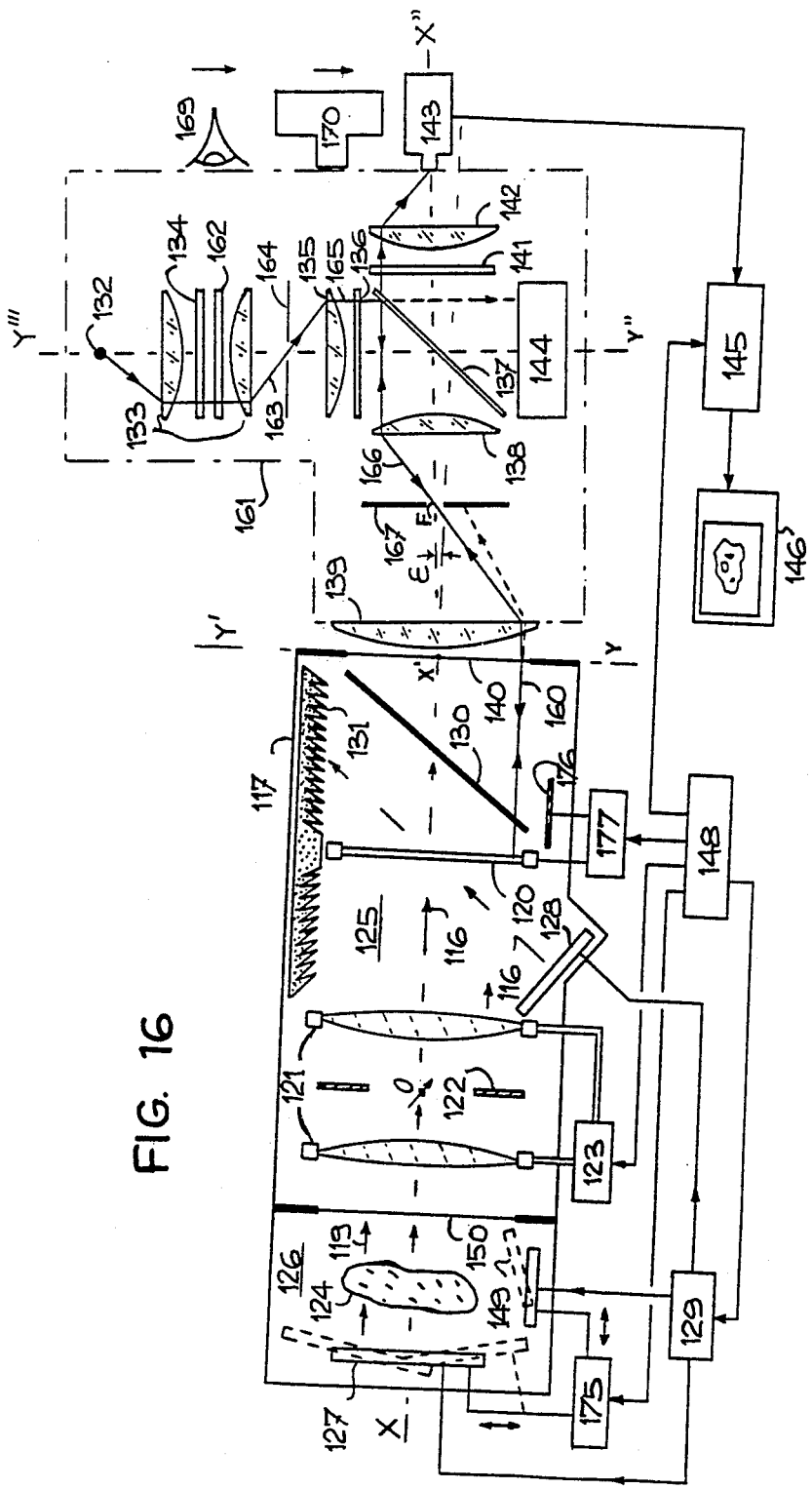

FIG. 16 is a diagram of a holographic ultrasonic camera incorporating a liquid crystal acousto-optical cell according to the present invention.

Figure 17:
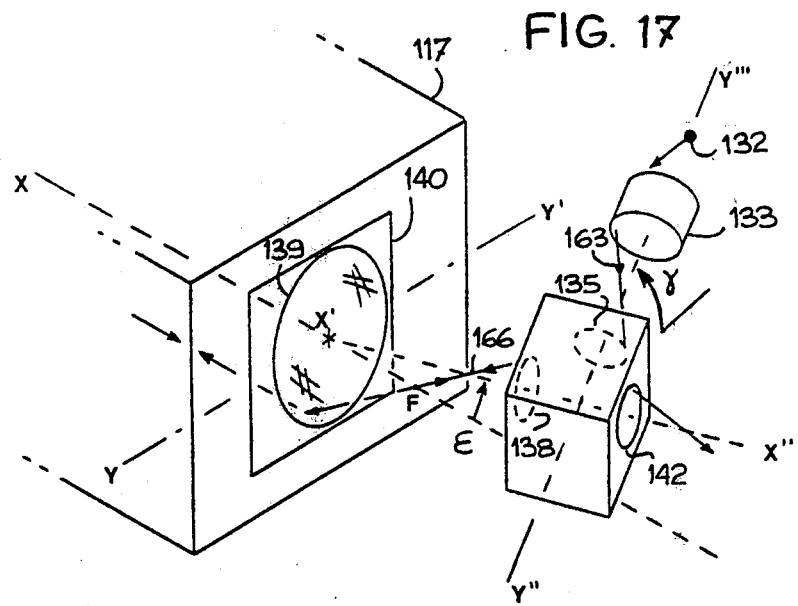

FIG. 17 is a detailed view of the ultrasonic camera of FIG. 16.

Figure 18:
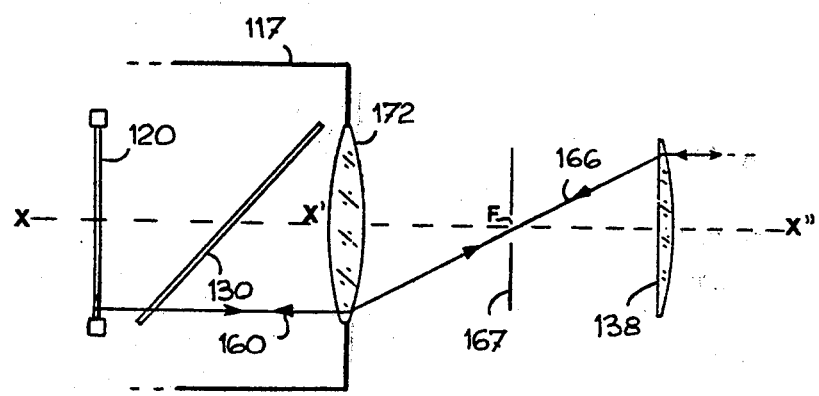

FIG. 18 shows a detail of a possible arrangement of the ultrasonic camera.

FIG. 19 illustrates the principle of a demodulation technique of the image-hologram given by the acousto-optical cell.

Figure 20:
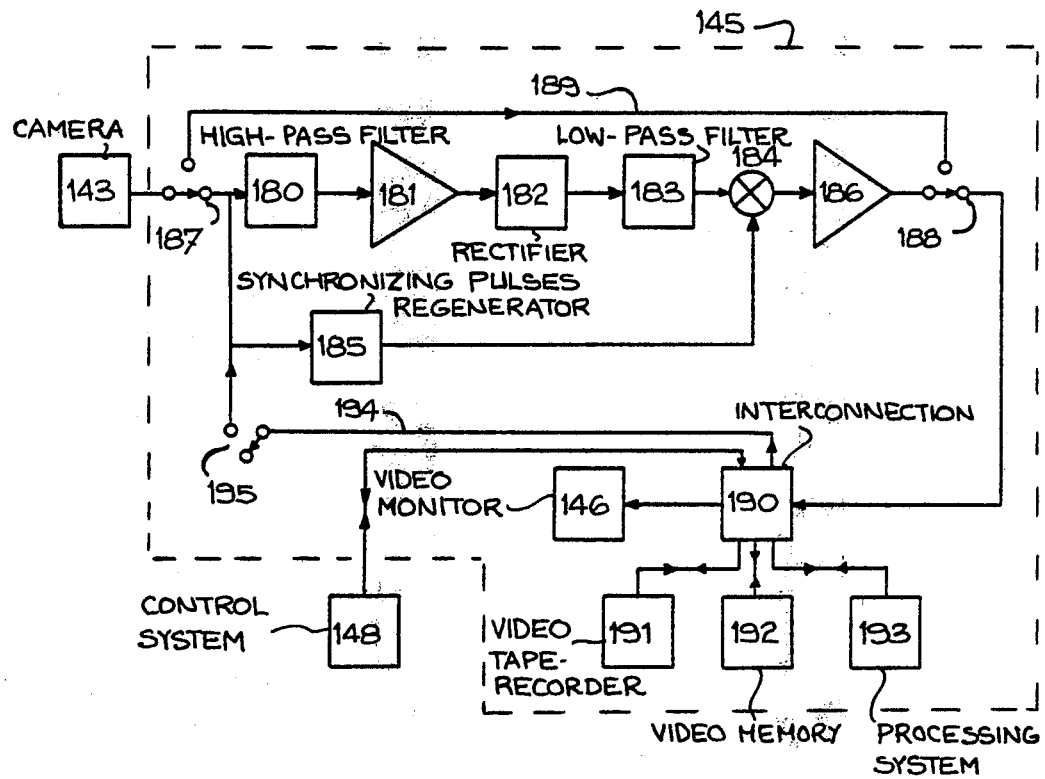

FIG. 20 is a diagram of an electronic demodulation system to process the acousto-optical hologram given by a cell.

Figure 21:
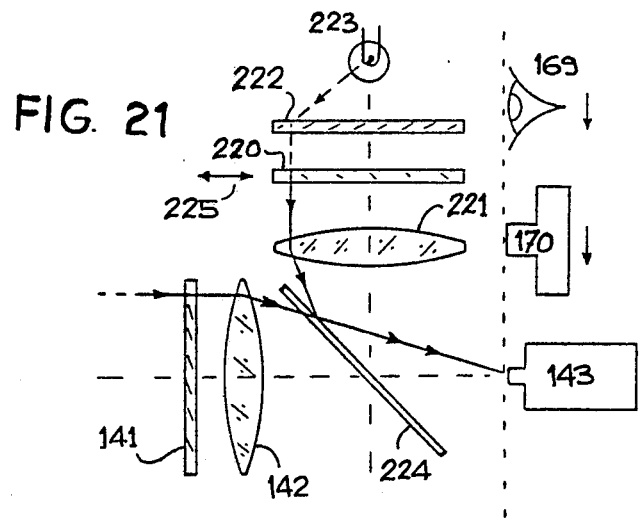

FIG. 21 illustrates a technique giving the phase image of an acoustical object by way of an acousto-optical cell.

Figure 22:
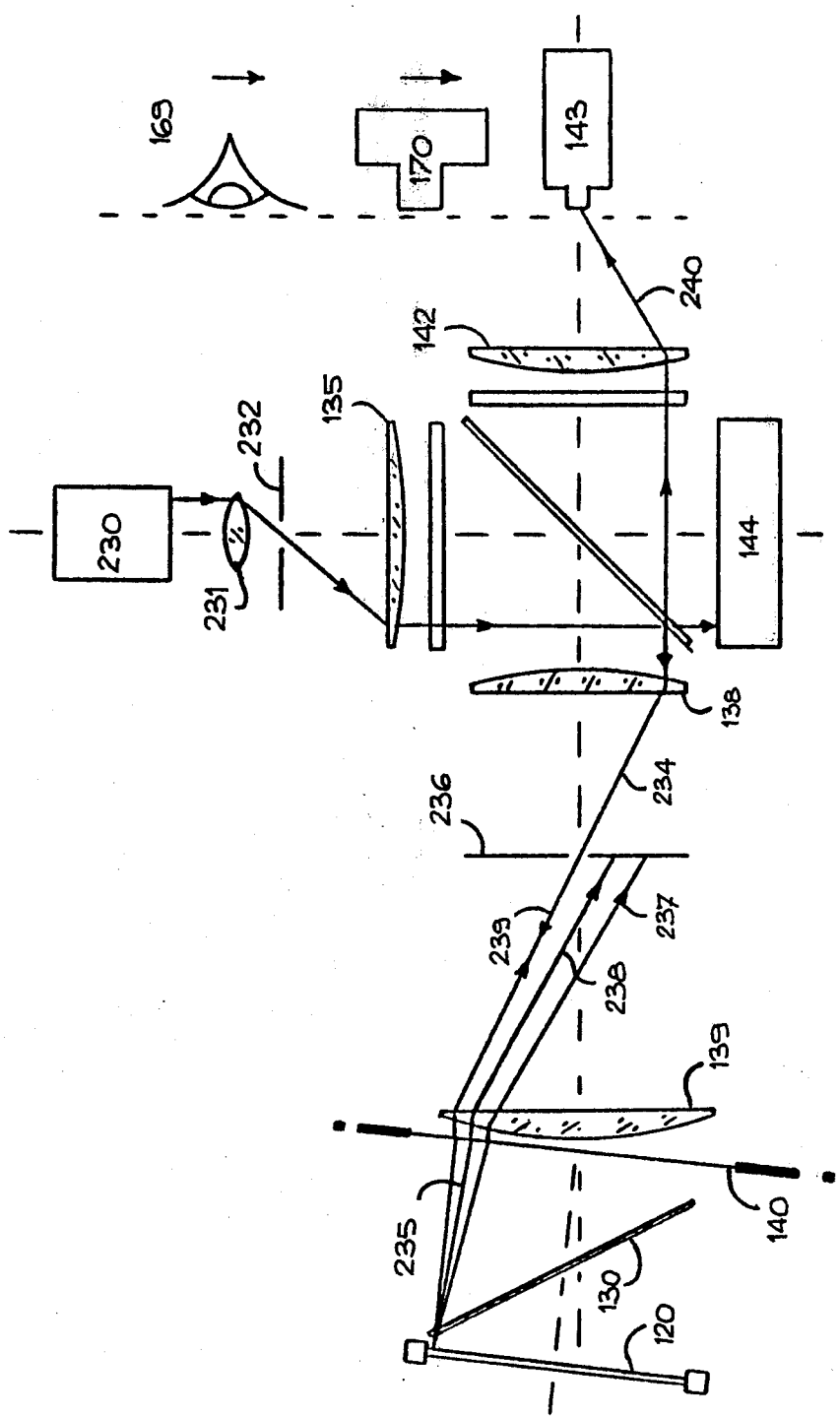

FIG. 22 shows still another embodiment of the present acousto-optical cells into a holographic acoustic camera.

Figure 23:
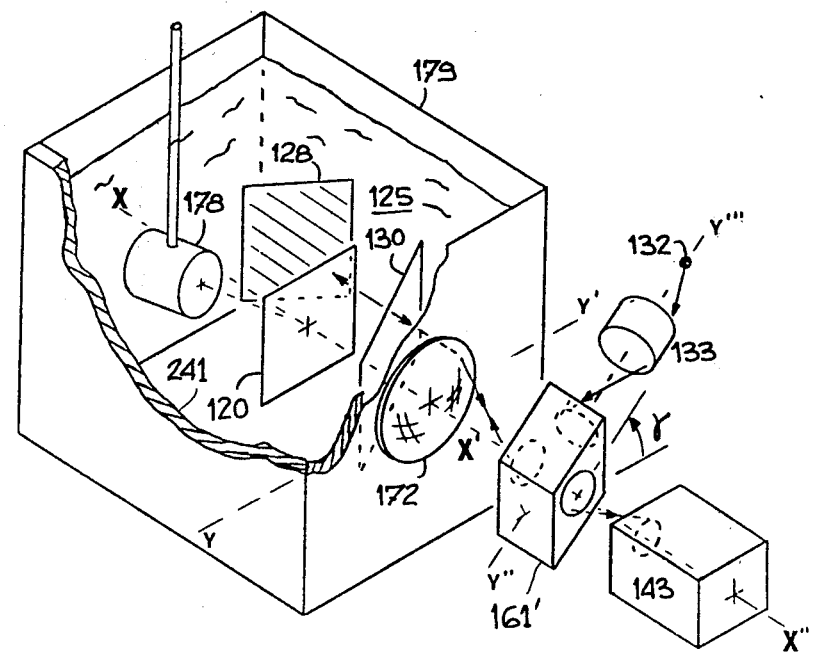

FIG. 23 represents a simplified system permitting acoustic imaging with an acousto-optical liquid crystal cell.

Figure 24:
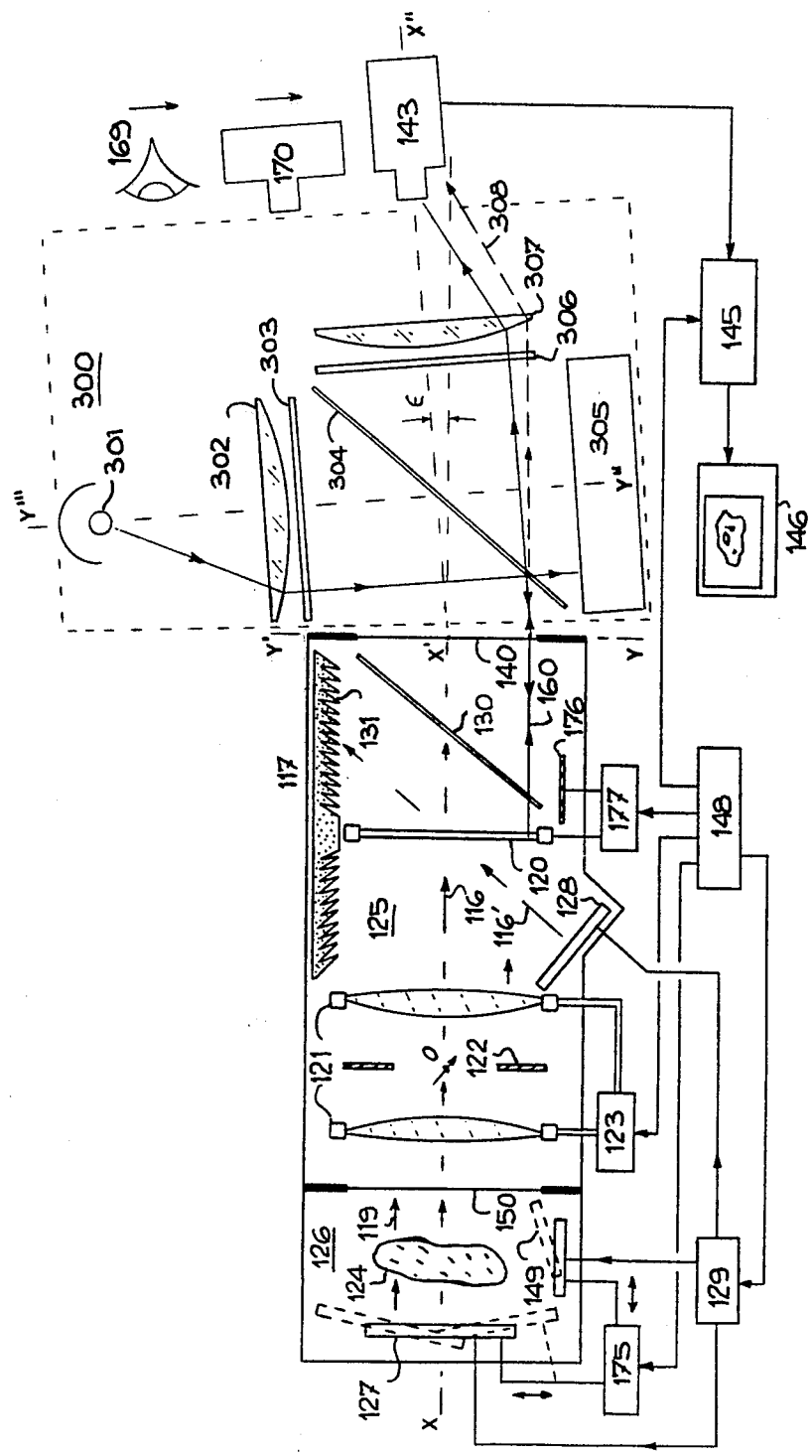

FIG. 24 shows another holographic ultrasonic camera incorporating a liquid crystal acousto-optical cell according to the present invention.

Figure 25:
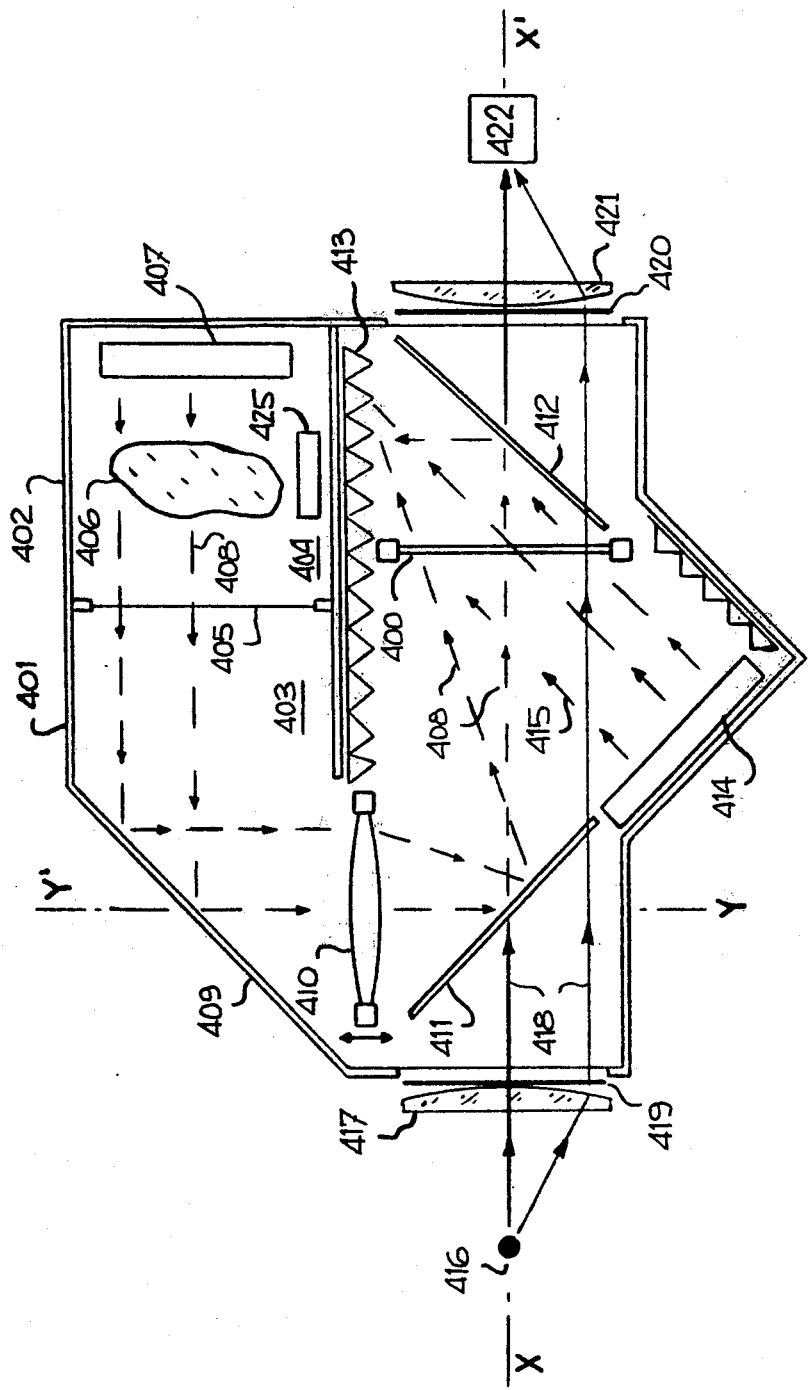

FIG. 25 represents a holographic ultrasonic camera incorporating a transparent liquid crystal cell.

If a thin layer of oriented liquid crystal is enclosed between walls transparent to ultrasonic waves, this form of energy induces a re-orientation of the molecules which can produce visible effects with the appropriate optical system. There exists a few different types of interaction between ultrasonic energy and a liquid crystal. A first type of interaction in a nematic liquid crystal was reported by L. W. Kessler and S. P. Sawyer, in Applied Physics Letters, vol. 17, No. 10 (1970). Other experiments of a different nature are particularly described by S. Letcher, J. Lebrun and S. Candau in Journal of the Acoustical Society of America, vol. 63, No. 1 (1978), p. 55. In this previous art, including the above mentioned Greguss cell, each cell wall was composed of only one glass sheet. As an effect, the width of the acoustic field was considerably limited in these cells: for angles of incidence differing from 0°, multiple reflections of acoustic waves occur between the walls, which produce streaming or turbulences in the liquid crystal, disordered re-orientations and undesirable visible effects.

The operating principle of the cell according to the present invention is based on an entirely different type of interaction between ultrasonic waves and a nematic liquid crystal, whereby the acoustic waves produce an ordered molecular re-orientation, without appreciable streaming in the liquid crystal. Furthermore, the visible effect becomes apparent for much lower acoustic intensities than in cells of the previous art. This effect can also be observed in other types of liquid crystals such as the cholesterics and the smectics. The operation of the present acousto-optical cell is not limited to any particular ultrasonic frequency, but generally gives remarkable results at frequencies between 0.5 and 15 MHz.

Figure 1:
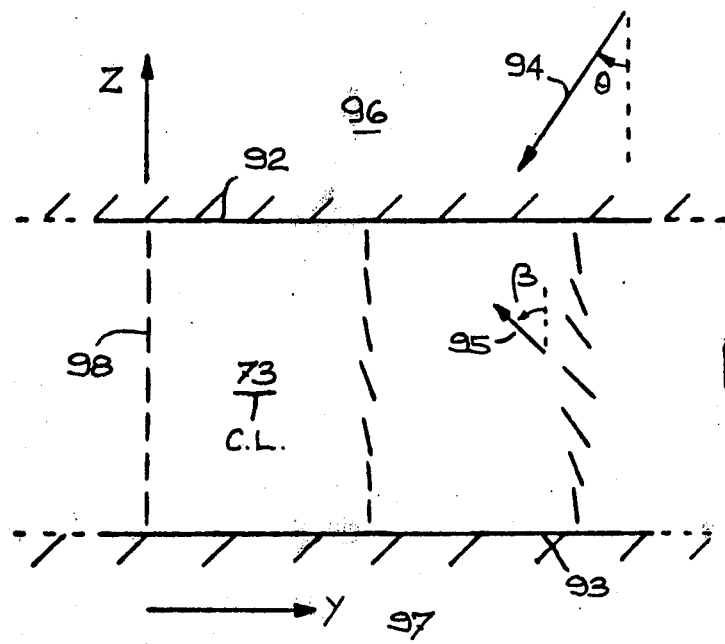
FIG. 1 shows schematically the effect of an ultrasonic wave on the orientation of liquid crystal molecules.

FIG. 1 shows a nematic liquid crystal layer 73, having initially a homotropic structure 98, that is with the molecules oriented perpendicular to the walls 92 and 93. An acoustic wave 94 is incident on the layer at an angle $\theta$, with its intensity I increasing in the "Y" direction. According to the new type of interaction used in the present invention, the long organic molecules of the liquid crystal (L.C.) have a tendency to become oriented perpendicular to the acoustic displacement, so minimizing the acoustic propagation losses. It was found that the torque M exerted on the molecular per unit volume is given by $$M = Cp^2 \sin 2\phi = C'I \sin 2\phi \tag{1}$$

where $\phi = \theta - \beta$ is the angle between the molecular axes and the mean direction of acoustic displacement or propagation direction of the acoustic wave, C and C' being constants depending on the particular type of liquid crystal used and its thickness, and p the acoustic pressure of the wave. If the molecules adjacent to the walls 92, 93 are firmly anchored, the structure of the liquid crystal 73 is distorted by an angle $\beta(z)$ as shown, where 95 indicates the maximum rotation in the middle of the layer. This rotation increases in the "Y" direction as indicated, with the ultrasonic intensity I, in a fairly proportional fashion. The relative absence of multiple reflections of acoustic waves between the walls is an essential condition for the production of a usable visible effect in the cell. These walls must therefore be highly transparent to acoustic waves 94. Consequently, the wall acoustic impedances must be matched to those of the adjacent propagation media 96, 97. If $Z_o$ is the characteristic acoustic impedance of the propagation medium on one side, and $Z_i$ the input impedance of the wall on the same side, it is well known that the reflection coefficient R for acoustic pressure is given by $$R = \frac{Z_i - Z_o}{Z_i + Z_o} \tag{2}$$

Figure 2:
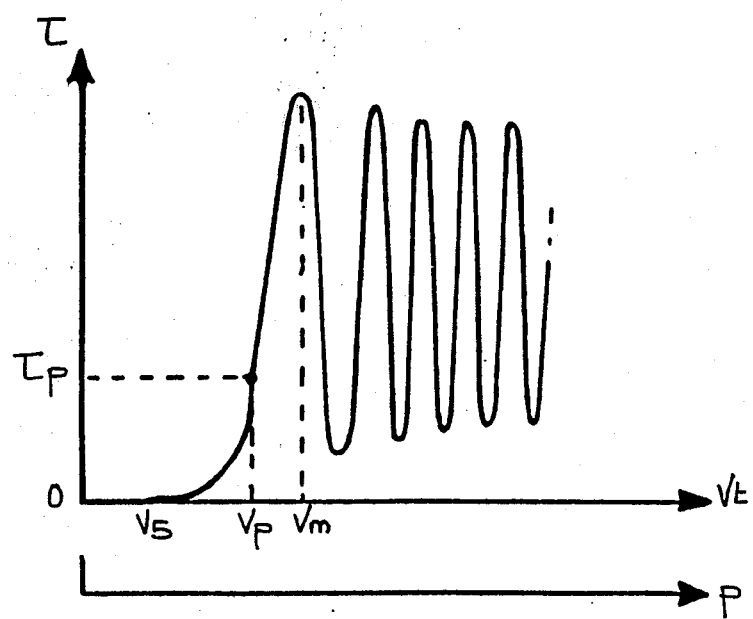
FIG. 2 shows the variation of light transmission through a liquid crystal acousto-optical cell as a function of the incident wave acoustic pressure.

R is generally a complex number and becomes null only when $Z_i = Z_o$. An essential characteristic of the present acousto-optical cells is to satisfy this last condition almost perfectly for widely varying angles of incidence $\theta$. The propagation media 96, 97 may be identical or different liquids. One of these media or both may even be solids, as long as condition $Z_i = Z_o$ is satisfied. Since the liquid crystal is a birefringent medium, this distortion modifies the state of polarization of light that simultaneously passes through. The following experimental facts have been discovered: light transmission $\tau$ through a homotropic nematic liquid crystal which is placed between crossed polarizers with axes oriented at 45° relative to the plane of incidence of acoustic waves varies as illustrated in FIG. 2, as a function of acoustic pressure p or voltage V applied to the ultrasonic transducers generating the waves. For $\tau \lesssim 0.5$ and incidence $\theta$ of about 45°, it is also found that $$\tau \approx K_1 p^8 \approx K_2 I^4 \tag{3}$$

where $K_1$ and $K_2$ are characteristic constants of a given L.C. cell, which also depend on the particular value of angle $\theta$. It has also been determined that for a given ultrasonic intensity I and angle $\theta$, the transmission $\tau$ varies with thickness a of the liquid crystal as $$\tau \approx K_3 a^{10} \tag{4}$$

for $\tau \lesssim 0.5$, where $K_3$ is a constant. In preferred embodiments of the present invention, a has usually a value comprised between 25 and 500 micrometers. One may say that there is a direct coupling between the wave vector of a compressional acoustic wave and the molecular axes of the L.C., producing the torque given by equation (1). Consequently, the intensity variations in the acoustic field corresponding to an image formed on the acousto-optical cell are directly transformed into a distortion of the L.C., so producing variations of transmitted light and therefore a visible image. The process is explained with more details below in relation with FIGS. 14 and 15.

FIG. 3 shows a preferred embodiment of the invention where the L.C. layer 73 is enclosed between rigid laminated or stratified walls 1, 2, 3 and 7, 8, 9. Layers 4 and 6 are very thin monomolecular layers of a surfactant which purpose is to confer the required orientation to the L.C. molecules. This well known technique of the art is particularly discussed in a publication by F. J. Kahn et al.: "Surface-produced Alignment of Liquid Crystals", Proceedings IEEE, vol. 61, No. 7 (1973), p. 823. A suitable surfactant to give alignment perpendicular to the walls (homotropic) is lecithin. Another is hexadecyl-trimethyl ammonium bromide and there are several others.

In the various embodiments shown here (FIG. 3 and similars), the propagation or coupling media 90, 91 are a same liquid which acoustic impedance is $$Z_o = \rho_o c_o \tag{5}$$

where $\rho_o$ is the density of the liquid, and $c_o$ is the velocity of sound in it. Water is a suitable coupling medium but is not exclusive. Most nematic compounds which have their mesophase or liquid crystalline phase centered on a temperature of about 20° C., can suitably be used in these cells. Such a compound is a eutectic mixture (50%—50%) of MBBA (p-methoxybenzylidene-p-n-butylaniline) and EBBA (p-ethoxybenzylidene-p-n-butylaniline) which has a negative dielectric anisotropy. Liquid crystals with positive dielectric anisotropy may also be used. Most L.C. commonly used have an acoustic impedance $$Z_c = \rho_c c_c \tag{6}$$

which is practically equal to that of water. In this case, the two walls of the cell should have comparable structures. In preferred embodiments, the structure is formed of a clear solid material 2 (or 8), of low acoustic impedance $$Z_2 = Z_8 = \rho_2 c_2 = \rho_8 c_8 \tag{7}$$

between identical layers 1, 3 (or 7, 9) of a solid clear material of impedance $$Z_1 = Z_3 = Z_7 = Z_9 = \rho_1 c_1 = \rho_3 c_3 = \rho_7 c_7 = \rho_9 c_9 \tag{8}$$

The value of $Z_2$ (or $Z_8$) is intermediate between $Z_o$ and $Z_1$ (or $Z_3$, $Z_7$, $Z_9$). The thickness of the various layers is a function of their acoustic impedance and the frequency of ultrasonic energy, as discussed below. Suitable materials for layers 1, 3, 7, 9 are, as an example, glass, fused quartz, or other materials with large acoustic impedance and stiffness, one of these two layers or both being possibly made of an optically opaque and reflecting material. In one possible embodiment, for example, where these materials are optically transparent, a metallic reflecting film 16 of aluminum or silver may be deposited on layers 7 or 8, such as to double the distance travelled by light 96 in the liquid crystal 73, by means of reflection. A suitable material for intermediate layers 2 and 3 is a polymeric film, glued to the other layers with a clear cement. This material may also be a clear polyester resin inserted between layers 1, 3 (or 7, 9), which polymerizes and hardens with time. FIG. 4 shows an assembling technique for this last structure. The sheets or slides 1 (or 7) and 3 (or 9) are deposited on optically flat glass plates 100, 101, on which they are closely and firmly held by a liquid film 102, 103 such as water, by means of the capillar effect. The edge is then sealed with varnish (nail polish) 104, 105. Spacers 106 determine the thickness of the polymeric resin. A sufficient quantity of this resin 107 (layer 2 or 3, FIG. 3) is then deposited on the lower assembly 3, 9, after which the upper assembly 1, 7 is lowered on spacers 106. If required, conductive film 15, 16 is deposited between layer 3, 9 and the resin. Electrical connection of 15, 16 with the outside is done by means of a metal strip 108 in contact with film 16. After complete hardening, the varnish is dissolved and removed, and the complete assembly is suspended in the same liquid that was used to make the slides 1, 7, 3, 9 adhere to the plates 100, 101. Infiltration of the liquid finally separates the different parts. A stratified plane wall is then obtained which is not birefringent, with dimensions that may be larger than $15 \times 15$ cm$^2$. The intermediate medium 2, 8 (FIG. 3) may also be a liquid, but the resulting wall should be weaker with a poorer thickness uniformity. In other embodiments, the material with higher acoustic impedance may inversely be placed between the layers of intermediate impedance. In still other embodiments, one of the optically transparent layers, or both, in opposite sides of the cell, may be composed of a polarizing material. In the case where the L.C. used is nematic and homotropic, both polarizers are then crossed. But their mutual orientation is in no way restricted to this, one, particularly if the liquid crystal structure is homogeneous (molecules parallel to the walls) or twisted, or still if a cholesteric or smectic L.C. is used. One of the transparent layer may also be birefringent and act as a retardation plate, quarter-wave or half-wave. A spacer 10

(FIG. 3) determines the thickness of liquid crystal 73. The whole structure is held together by frames 5 and 12 which may be bolted with 14 and sealed or cemented with epoxy or silicone cement. These frames may be made of metal, ceramic or plastic.

The acoustic transmission coefficient of such layered walls can be determined by classical formulas which may particularly be found in the book titled "Waves in layered media", by L. M. Brekhovskikh (Academic Press, New York, 1960). Referring to FIG. 5 which represents a triple layered wall with materials of acoustic impedances $Z_1$, $Z_2$, $Z_3$, and thickness $d_1$, $d_2$, $d_3$, between propagation media 90, 73 with impedances $Z_o$, $Z_c$, then the input impedance $Z_i$ of the structure for an acoustic wave 94 is a complex variable function $$Z_i = g(Z_o, Z_1, Z_2, Z_3, Z_c, c_o, c_1, c_2, c_3, c_c, d_1, d_2, d_3, f, \theta) \quad (9)$$

where f is the wave frequency. The reflection coefficient R is given by formula (1), and the modulus of the transmission coefficient is consequently $$|T| = (1 - |R|^2)^{\frac{1}{2}} \quad (10)$$

In usual embodiments of the present invention, $Z_o \approx Z_c$, $d_1 \approx d_3$, $Z_1 \approx Z_3$, and $Z_o < Z_2 < Z_1$. In this case, it is experimentally verified that at a given frequency f, transmission T at normal incidence $\theta = 0°$ is essentially 100% for a certain minimum thickness $d_2$ of the intermediate layer. Furthermore, acoustic transmission T reaches nearly 100% for widely varying angles of incidence. An essential feature and property of the various embodiments of the present invention is an acoustic transmission of nearly 100% for angles of incidence between $-12°$ and $+12°$ and in the vicinity of $\pm 45°$, as shown in FIG. 6. It follows that there are practically no stationary waves in the L.C. 73, such as the previously described effect of ultrasonic energy is produced and becomes visible for acoustic intensities I of less than 100 $\mu W/cm^2$, without artifacts due to streaming. Another important advantage of these stratified cell walls is their strength: for the same thickness as a single glass sheet, they have a much higher resistance to stresses and shocks, for example. At an operating frequency of 3 MHz, the different layers have a thickness $d_1$, $d_2$, $d_3$ of the same order, $d_1$ and $d_3$ being comprised between 100 and 200 $\mu m$, and $d_2$ between 15 and 125 $\mu m$.

A remarkable feature of the various embodiments of the invention is the fact that maximum acousto-optical effect in the L.C. is possible due to the high acoustic transmission of the cell walls. Referring to FIGS. 1 and 3, we see that an ultrasonic wave passing through the layered walls of the cell will produce a tilt or rotation $\beta(z)$ of the L.C. molecules depending on the torque given by eq. 1. The effective optical birefringence of the medium is therefore modified, so producing a phase shift $\Phi$ between the ordinary and extraordinary components of the light wave 96 going through the L.C. Knowing the distortion $\beta(z)$, it is possible to compute $\Phi$ and the transmission of light $\tau$ through the L.C. layer by the following formula known in optics:

$$\tau = \sin^2 2\gamma \sin^2 (\tfrac{1}{2}\Phi) \quad (11)$$

where $\gamma$ is the angle between the polarization plane of incident light and the plane determined by the axis of the molecules and the normal to the layer. This equation shows that a variation of light transmission through the L.C. layer is a consequence of acoustic energy producing a distortion $\beta(z)$ of the molecular structure which produces a phase shift $\Phi$ between light components. This light may be monochromatic or quasi-monochromatic, and in many cases white light is suitable. The liquid crystal cell shown in FIG. 3 may incorporate a reflecting layer 16 of negligible thickness. In this case, light waves 96 incoming from propagation medium 90 will travel twice the layer thickness, and the phase shift $\Phi$ will be doubled. Equation (11) shows that for small values of $\Phi$, light transmission $\tau$ will be four times as large as in a non-reflecting cell, since $\tau$ is then proportional to the fourth power of $\Phi$. Consequently, an acousto-optical cell with a reflecting layer 16 (FIG. 3) is preferable for higher sensitivity to ultrasonic energy.

FIG. 7 represents another embodiment of the L.C. acousto-optical cell where an electric field is produced inside the liquid crystal layer 73 in such a way as to quickly re-orient the molecules which have a positive dielectric anosotropy, after having been disturbed from their original position. This field is created by electrically conductive deposits 15, 16, of which at least one (15) is optically semitransparent. They are connected to an alternating voltage source 17 through switch 27. The frequency used is in general between 50 Hz and 25 kHz, with voltages between 2 and 200 volts. In all other aspects, this embodiment is similar to the one shown in FIG. 3. If the molecular axis is normally perpendicular to the cell walls (homotropic or homeotropic structure), this orientation will be restored if the L.C. has a positive dielectric anisotropy ($\epsilon_{11} - \epsilon_1$), where $\epsilon_{11}$ is the electric permittivity parallel to the molecular axis, and $\epsilon_1$ is the electric permittivity perpendicular to the molecular axis.

As shown in FIG. 8, it is also possible to eliminate one of the electrodes 15 or 16 in other embodiments. In these, the semi-transparent electrode 15 of FIG. 7 is suppressed and replaced by an external electrode 176 (FIG. 8) in the liquid propagation medium 90. This liquid being preferably moderately ionized, a relatively high fraction of the voltage drop appears across the L.C. layer 73, so creating an alternating electric field E to re-orient the L.C. molecules when power supply 17 is connected through switch 27.

FIG. 9 shows still another embodiment of the acousto-optical L.C. cell operating on the same principles and having the same advantages as those of FIGS. 3 and 7, except that the walls have a larger number of solid layers, and the structure is therefore more resistant. The wall composed of principal layers 20, 19, 18, 2, 3 (or the other: 7, 8, 21, 32, 33), with electrodes 15, 16 and the surfactant layers 4, 6 which have negligible thickness, are equivalent to the superposition of two walls such as 1, 2, 3 in FIG. 3. So, in a preferred embodiment as in FIG. 9, the thickness of 18 (or 21) will be twice that of 20 and 3 (or 7 and 33), in the case where media 90, 73, 91 have substantially the same acoustic impedance. As a function of the angle of incidence, the acoustic transmission T of such a structure is substantially the same as the one indicated in FIG. 6. Electrodes 15, 16 have the same purpose as in FIG. 7: re-establish the original orientation of the liquid crystal molecules by producing an electric field. It is also possible to suppress one of these electrodes 15, 16 in certain embodiments as explained above in relation with FIG. 8. Still other embodiments according to FIG. 9 may incorporate light polarizing layers in opposite walls, in place of one layer shown in each wall. One of these layers, in still other embodiments, may be an optical wave retardation plate, as mentioned above.

FIG. 10 represents an embodiment of the present invention, where the liquid crystal cell incorporates a matrix or array of integrated semi-conductor photodetectors 22 which can directly deliver electrical signals corresponding to the acoustic field in the liquid crystal layer 73. As in the preceding embodiments, the input acoustic impedance $Z_i$ of the cell is matched to those of the propagation media 90, 73, 91, by means of stratified walls, so that acoustic energy 94 passing freely through the cell exerts a maximum distorting action on the molecules of liquid crystal 73. One of the layers in the input wall, 1, 2, or 3, may incorporate a polarizing material such as a suspension of dichroic molecules, to polarize the incoming light. One of layers 7 or 8 in the opposite wall is made of a polarizing material which axis is perpendicular to that of the other polarizer, such that when the L.C. molecules 73 are in the normal state, substantially no light can reach the photo-detectors 22. One of the layers between these polarizers may also be composed of a birefringent material acting as a half-wave or a quarter-wave retardation plate. Therefore, the acoustic energy 94 (FIG. 10) passing through liquid crystal 73 causes a structure distortion that modifies the polarization state of light waves 96 also passing through 73. This perturbation is translated into an intensity change of light 96 that reaches the detector array 22 when the relative orientation of the polarizing layers is appropriate. Without intermediate birefringent layers, using a homotropic nematic liquid crystal 73, the polarizers should be crossed. The detectors 22 can be an array of photodiodes, phototransistors, photoresistors or any other type of light detectors known in the field of integrated circuits, including charge transfer devices. This array or matrix 22 is generally composed of m x n elements connected to multiple conductors 24, 25, transmitting to an outside electronic system the signals generated by each detector element, in both dimensions X and Y.

FIG. 11 shows another embodiment of the invention where maximum torque interaction is produced between incident acoustic energy 94 and the liquid crystal layer 73 according to equation (1). In this embodiment, the acousto-optical cell walls are made of polymeric membranes 70, 76, tensioned and cemented on frames 78, 79. The frames can be united by bolts 81 and sealed by cement 80. A very thin layer 71 (or 75) of vacuum or chemically deposited inorganic material, such as magnesium fluoride, allows anchoring of a thin surfactant layer 72 (or 74) which induces the required L.C. molecules orientation 73. Spacer 77 determines the thickness of the L.C. layer 73. Membranes 70, 76 may also be composed of polarizing material which axes are crossed if liquid crystal 73 is a homotropic nematic compound layer. If the membrane thickness is substantially smaller than a quarter wavelength of acoustic waves in this material, a large fraction of this energy will be transmitted through the cell for widely varying angles of incidence. Layer 75 can also be metallic and act as an optical mirror, vacuum deposited aluminium for example. In this case, the optical path of light waves 96 is doubled, and the sensitivity of the cell is four times as large as that of a non-reflecting cell, as explained above.

FIG. 12 represents another embodiment where layers 71, 75 of FIG. 11 are replaced by electrodes 82, 83, of which at least one, 82, is semi-transparent. Their purpose is to produce in the liquid crystal 73 an electric field when they are connected to the voltage supply 17. This field rapidly restores the initial orientation of the molecules, as explained above in relation with FIG. 7. In all other respects, this embodiment is identical with the one shown in FIG. 11.

Another embodiment shown in FIG. 13 is similar to those of FIGS. 11 and 12, except that membranes 70, 76 are replaced respectively by membranes 84, 85 and 86, 87. One of the adjacent membranes can act as a polarizer, while the other can act as an optical phase retardation plate, or can be simply isotropic according to the desired effect. In all other respects, this L.C. acousto-optical cell or convertor is similar to those represented in FIGS. 11 and 12.

FIG. 14 shows the effect of two longitudinal and mutually coherent ultrasonic waves 200, 201, on the orientation of a liquid crystal layer 202, when the original orientation of its molecules is perpendicular to the walls (homotropic structure). In general, the vibrational movement of the molecules is elliptical (203) because of the phase difference between the vibrations of 200 and 201. It has been experimentally proved that in this case, the molecules tend to become oriented with their long axis (or director axis) substantially in the direction of the miror axis 204 of the elliptic movement. More generally, the molecules tend locally to become oriented in a direction such as the acoustic losses be a minimum. Such a direction exists in a liquid crystal because of the anisotropy of its viscosity. In certain points such as A, vibrations 205A, 206A corresponding respectively to waves 200, 201, are in phase and the molecular displacement 207A is rectilinear. As a consequence, the molecules tend to re-orient in direction 208A perpendicular to 207A. At point B located half-way between two adjacent points A, vibration 205B is 180° out of phase relative to 205A and 206A and 206B are in phase. Therefore, the resulting vibration direction 207B is different from 207A. The resulting molecular axis direction is then substantially 208B, which is different from 208A. So, under the influence of acoustic interference, there is a spatial modulation of the direction of the L.C. molecular axes, accompanied by a consequent spatial variation of the medium optical properties. These variations can be made visible by means of various suitable systems, as those described below.

FIG. 15 illustrates the effect of these molecular re-orientations on polarized light transmitted by the liquid crystal. The re-orientation 204 of the L.C. molecules 202 taking place in the figure plane, the cell is placed between crossed polarizers 210, 211, with polarization axes inclined at 45° above the plane of the figure. Under these conditions, the incident light waves 212 come out of the liquid crystal 202 with elliptical polarization 213 when the L.C. molecules are disturbed from their normal orientation. Therefore, the intensity I of light 214 transmitted by analyser 211 varies periodically as shown by the graph of I as a function of x, the position in the cell. The spatial modulation of direction of the L.C. molecules are therefore converted into spatial variations of light intensity: ultrasonic interference fringes can then be directly visualized as luminous fringes. If an ultrasonic (or acoustical) hologram is formed in the L.C. layer of one of the embodiments of the present invention, this hologram is directly and instantaneously transformed into an optical hologram.

FIG. 16 shows a system incorporating a nematic liquid crystal acousto-optical cell of the reflection type made according to any of the above mentioned embodiments of the invention. The whole system constitutes a holographic ultrasonic camera having the possibility of visualizing various bodies and their inside by transmission or scattering of ultrasonic waves. The system can take the acoustical imagehologram of an object and of its internal structures and convert it directly, and in real-time, into an optical imagehologram. Another particular feature of this camera is to be able to convert this last hologram into an image of the object by means of electrical signal processing. In one particular embodiment, it is also possible to obtain at will an acoustical intensity image or an acoustical phase image.

The main enclosure 117 is filled with a liquid 125 which may be water or any other liquid that easily propagates ultrasonic waves. The nematic liquid crystal cell of the reflecting type 120 is substantially perpendicular to the aixs XX' of the system. A system of hydro-acoustic lenses 121 which are inflatable by means of a pump 123, with aperture 122, focuses on cell 120 the acoustic waves 119 coming from a transversal plane of the object to be examined 124. This object may be situated in a different liquid medium 126, separated from medium 125 by an acoustically transparent polymeric membrane 150.

A large surface ultrasonic transducer 127 generates waves which are substantially plane for transmission examination of object 124. If necessary, the transducer may be in contact with the object. Another transducer 149 can be used separately for lateral insonification of 124. In this last case, acoustic energy scattered by the different parts of the object is used to form the acoustic image on cell 120. The same transducer can also be used alternately in both positions 127 or 149. Transducer 127 for transmission imaging can rotate with two degrees of freedom about a point in the vicinity of center 0 of acoustic lenses 121. Transducer 149 for scattered wave imaging could also rotate in the same fashion about a point in the vicinity of object 124. These movements allow phase shifting of the acoustic waves coming from different points of the point and appreciable reduction of image artefacts due to wave coherence, by a method explained below. Another transducer 128 is used to generate a plane acoustic wave 116' with substantially uniform intensity that passes through the acousto-optical cell 120 and produces a general reorientation or pre-orientation of the L.C. molecules. These transducers are driven by a same RF generator 129 through possibly separate amplifiers for each transducer, so that they produce coherent ultrasonic waves that interfere on cell 120. Consequently, the image-hologram of a transversal plane of object 124 is formed on the acousto-optical cell 120, because of the spatial modulation of molecular orientation described above in relation with FIGS. 14 and 15. The largest part of acoustic energy coming from lenses 121 passes freely through cell 120 and is reflected by an optically transparent glass plate, or a plate made of any other optically transparent and isotropic material 130 making an angle of about 45° relative to cell 120. The reflected acoustic energy is then received by an absorber 131. This absorber can be made of an acoustically absorbent material such as rubber, with acoustic impedance matching that of liquid 125. In the same way, most of the acoustic energy coming from pre-orientation transducer 128 and going cell 120 is then absorbed by 131. The fraction of the acoustic energy reflected by 120 is also absorbed by the portion of 131 extending in front of 120. In both cases, the absorbing prisms are oriented towards the incoming acoustic energy.

In the embodiment of FIG. 16, the plane light waves 160 used to obtain the optical hologram corresponding to the acoustical hologram, travel on the side of cell 120 opposite to the acoustic lenses 121. The light waves go through the L.C. layer of reflection cell 120 with substantially normal incidence and are reflected in approximately the same direction back to the external optical system 161 where they come from. This configuration however is only one of several possible ones. In other embodiments of the invention, for example, the light waves could propagate on the same side as the acoustic lenses 121. In this case, the use of acoustically transparent optical mirrors, or optically transparent acoustical mirror would be required. In other embodiments, acousto-optical cell could be transparent to light, and optically transparent acoustical mirrors would be needed, or possibly acoustically transparent optical mirrors. The light waves can originate from a point-like source of coherent or incoherent light 132 associated with condenser 133. This condenser can particularly incorporate an infrared blocking filter 134, a colored filter or interferential filter 162, or any other appropriate type of optical filter. The conical beam 163 passing through aperture 164 is refracted by lens 135 which gives a substantially cylindrical light beam 165, linearly polarized by filter 136. The polarizing axis of this filter must be parallel or perpendicular to the plane determined by axes X''X'' and Y''Y''' of the optical system. Axis Y''Y''' is preferably set at an angle $\gamma$ above the plane of the figure containing axes XX' and YY'. Angle $\gamma$ is to be found in equation (11) and is preferably chosen to be 45° or 135°. FIG. 17 gives details of this arrangement. Light beam 165 (FIG. 16) is divided in two parts of nearly equal intensities by beam splitter 137. One part is lost in light trap or black body 144. The other part is refracted into a conical beam 166 by lens 138. The focal points of lenses 138 and 139 are coincident at F. Conical beam 166 passing through aperture 167 becomes cylindrical after being refracted by collimating lens 139. As shown in FIG. 18, a collimating lens 172 set into the enclosure wall 117 can, at the same time, act as a refracting element like lens 139 and as a water-tight opening. In this case, axis X'X'' of the optical system can coincide with axis XX' of the acoustical part of the system.

Referring now to FIG. 16, cylindrical light beam 160 goes through the liquid crystal layer of cell 120, is reflected on cell wall with a reflecting deposit, and goes back in substantially the same direction. Its polarization is then generally elliptical. This light passes through lens 139 in the opposite direction, and converges towards aperture 167 and lens 318. The light beam becomes substantially cylindrical after refraction by lens 138 and is then partially transmitted by beam splitter 137. A polarizer or analyser 141 with its polarization axis substantially perpendicular to that of polarizer 136 normally extinguish the light beam when the liquid crystal in 120 is at rest, with no acoustical image being formed on the cell, since there is then no modification of polarization of light passing through the cell. Light passing through polarizer 141 is refracted by lens 142 towards an appropriate detector such as an observer's eye 169, a photographic camera 170, a video camera 143 or any other convenient detector. The aperture or entrance pupil of the detector is approximately coincident with the focus of exit lens 142. The focusing of detector 169, 170, 143 or any other is done on the image of the cell 120 given by window 140 and lenses 139, 138 and 142. Axis X'X" of the optical system 161 makes an angle ε of a few degrees with axis XX', in the drawing plane or in a near plane, such that the fraction of light energy reflected by entrance window 140 of enclosure 117 is stopped on its way back by aperture 167.

In FIG. 16, block 148 represents the central control system of the various functions associated with the liquid crystal convertor ultrasonic camera.

FIG. 19 illustrates the various steps required to obtain the acoustical image-hologram of an object and convert it to a visible image. FIG. 19-a represents the intensity distribution of the acoustical image formed by lenses such as 121 (FIG. 16) in the plane of cell 120: in area MNPQ, intensity is uniform and higher than in the surrounding area; AB is a scanning line. The image-hologram seen on 120 through optical system 161 by a detector like 169, 170, 143 or other (FIG. 16), is represented in FIG. 19-b. Area MNPQ corresponds to interference fringes of higher contrast than those of surrounding area. This hologram may be considered as a spatial carrier of period b which amplitude is modulated by acoustic intensity and which phase or position is modulated ($\Delta x$) by the phase of acoustic waves coming from the object. FIG. 19-c shows one period or scan line of the video signal corresponding to line AB, such as given by video camera 143 of FIG. 16. The spatial carrier with period b along line AB corresponds to the time domain carrier of period $T_o$ or frequency $f_o$, which amplitude A(t) is modulated by the contrast of the hologram fringes, and which phase $\psi(t)$ is modulated by position $\Delta x$ of the hologram fringes. In time interval $t_o$-$t_1$, the video signal is approximately described by $$v(t) = C(t) + A(t) \cos [2\pi f_o t + \psi(t)] \quad (12)$$

where C(t) is a mean value with slight variation in the interval. The synchronisation pulses of the video signal are designated by S.

This video signal is fed to a processing system 145 (FIG. 16) which can provide a fringe-less visible image such as illustrated in FIG. 19-f. FIG. 20 shows the principal components of this processing system which we consider exclusive to the present invention. The video signal (FIG. 19-c) from camera 143 is fed to the highpass filter 180 which cut-off frequency is about $f_o/2$, and is then amplified by 181: at this point, its form is as shown in FIG. 19-d. This signal is fed to rectifier 182, associated to low-pass filter 183 which cut-off frequency is approximately equal to the fundamental frequency of the rectified signal. At the output of this filter, the signal is as shown in FIG. 19-e. Adding circuit 184 (FIG. 20) superposes the signal of FIG. 19-e and the synchronizing pulses lost in the filtering process and regenerated by circuit 185. The signal is then amplified by 186 and fed to a selector 190. Switches 187, 188 allow by-passing the demodulation system by path 189 and feeding the image-hologram signal directly to monitor 146. Central control system 148 (FIGS. 16 and 20) allows interconnection of various elements through 190, such as video monitor 146, video tape recorder 191, video memory 192, computerized image and hologram processing system 193, or any other useful sub-systems. The demodulated signal coming out of 186 (FIG. 20) gives on monitor 146 an image such as illustrated in FIG. 19-f where high brightness area M'N'P'Q' corresponds to high ultrasonic intensity area MNPQ of FIG. 19-a. FIG. 19-g shows the image-hologram obtained when no object is placed in front of transducer 127 in FIG. 16: it may be called the "background hologram". On AB, in interval $t_o$-$t_1$, the expression of the video signal corresponding to this last hologram is approximately $$V_o(t) = C_o + A_o \cos 2\pi f_o t \quad (13)$$

This background or "reference" hologram is particularly useful to obtain the acoustic phase image of the object with the present invention. If, in a first operation, a background hologram is taken and stored in video memory 192 or other 193 and then, in a second operation, the image-hologram of the object taken and superposed to the background hologram in the memory, we obtain the interferential hologram of the acoustic object. Along line AB of such a hologram, the corresponding video signal may be expressed approximately as $$v'(t) = C_o + C + A_o \cos 2\pi f_o t + a \cos [2\pi f_o t + \psi(t)]$$

or $$v'(t) = C'(t) + A'(t) \cos [2\pi f_o t + \psi'(t)] \quad (14)$$

where the term $C'(t) = C_o + C$ is practically constant and, as easily demonstrated:

$$tg \, \psi'(t) = \frac{A \sin \psi(t)}{A_o + A \cos \psi(t)} \quad (15)$$

and $$A'(t) = [A_o^2 + 2A_o A \cos \psi(t) + A^2]^{\frac{1}{2}} \quad (16)$$

These equations show that the fringe contrast in the interferential image-hologram, as measured by amplitude A'(t), is a function of the fringe position in the hologram of the object and therefore a function of the phase of acoustic waves coming from the various points of the object, because $\psi(t)$ is directly a function of the fringes position. The interferential hologram can be seen and interpreted directly on video monitor 146 (FIG. 16), or it is possible to obtain the fringe-less phase image by applying the video signal (Eq. 14) to the input 180 of the demodulation system (FIG. 20) through path 194 and switch 195.

The acoustical interferential holograph just described has the outstanding feature of being able to image in a unique and remarkable way very small changes that have taken place in a given object, which is relatively transparent to ultrasonic energy, between two consecutive instants, or to make visible very small differences between two apparently identical objects. Suppose, for example, that an acoustical hologram is taken of the object with system of FIG. 16, or similar ones incorporating a L.C. acousto-optical convertor according to the present invention, and stored in a video memory 192 (FIG. 20). As previously, the signal corresponding to a line of this hologram is approximated by $$v_1(t) = C_1 + A_1(t) \cos [2\pi f_o t + \psi(t)] \quad (17)$$

If now, a second hologram is taken of the same object at the same place, but which has been slightly deformed in the meantime, or still, the acoustical hologram of an apparently identical second object, exactly at the same place. This second hologram which is more or less different from the first, according to the structural differences or others which have intervened, is such that the video signal corresponding to a line is approximated by $$v_2(t) = C_2 + A_2(t) \cos [2\pi f_o t + \psi(t) + \Delta\psi(t)] \quad (18)$$

If the second hologram is substracted from the first, the corresponding line becomes, after some algebric operations, $$v_3(t) = (A_1 - A_2 \cos \Delta\psi) \cos (2\pi f_o t + \psi) + A_2 \sin \Delta\psi \sin (2\pi f_o t + \psi) \quad (19)$$

This may be written as:

$$v_3(t) = b(t) \cos [2\pi f_o t - \delta(t)] \quad (20)$$

It has been supposed that $C_1 \approx C_2$. Phase variation $\Delta\psi(t)$ measures the shift of a fringe in the second hologram relative to the first hologram: it is a function of the phase difference of acoustic waves coming from the same points of an object at two different times, or from corresponding points of two different objects successively placed at the same location. It is easily shown from the preceding equations that the amplitude of the resulting signal $v_3(t)$ is given by $$b(t) = [A_1^2 - 2A_1 A_2 \cos \Delta\psi(t) + A_2^2]^{\frac{1}{2}} \quad (21)$$

This equation shows that the amplitude b(t) of the video signal corresponding to the resulting interferential acoustical hologram is a function of perturbations $\Delta\psi(t)$, caused by very small possible differences between two successive states of the same object at the same place, or between two slightly different objects successively at the same location. As mentioned above, this difference hologram or interferential hologram may be observed and interpreted directly on video monitor 146 (FIG. 16), or a fringe-less image of differences may be obtained by processing video signal $v_3(t)$ through 180–186 (FIG. 20) by way of path 194 and switch 195. Phase $\delta(t)$ of the signal (eq. 20) is given by $$tg\ \delta(t) = \frac{A_2 \sin \Delta\psi(t)}{A_1 - A_2 \cos \Delta\psi(t)} \quad (22)$$

This difference image produced by interferential acoustical holography can be obtained by other methods exposed below. It is also a remarkable fact that with these techniques made possible by the liquid crystal acousto-optical cell, it is possible to subtract the distorting effect of a perturbating medium between the object to be examined and the camera: a first hologram is taken of the perturbating medium without the object, and the second hologram taken with the object is then subtracted from the first as described above. It is possible this way to obtain much clearer images than with the previous art. It is possible a remarkable feature of the present invention that phase perturbations $\Delta\psi(t)$ can electronically modulate a color video signal in such a way as to obtain a so-called "pseudo-color image", which gives very interesting and useful additional information on objects examined by means of ultrasonic energy.

Another way of obtaining the intensity or phase image of an acoustical object with the present invention consist in sending video signal from camera 143 (FIG. 20) through electrical path 189 directly to a computerized image processing system 193 using the appropriate fast Fourier transform algorithm.

Still another practical way to obtain the phase image of an acoustical object consists is recording the background or reference hologram on photographic film by means of a camera 170 (FIG. 16) and superposing the developed hologram to the image-hologram of the object by optical means. This can be done in particular with the accessory represented in FIG. 21 which is associated to the optical system of FIG. 16. The background hologram, previously photographed with camero 170 is placed after development in the vicinity of the focal plane of lens 221 which forms an image of it on the clear background of screen 222 lighted from behind by lamp 223. By means of beam-splitter 224, this image of the background hologram is superposed to the image-hologram seen through exit lens 142 of optical system 161. The exact superposition can be achieved by making coincident the images of guiding-marks RSTU (FIG. 19-g) located on L.C. acousto-optical cell 120 (FIG. 16). An appropriate detector such as 143, 169, 170, or any other appropriate one, can then record the interferential image-hologram of the acoustical object. A phase image of this object can be obtained by demodulating, as explained above, the signal given by video camera 143 by means of demodulation system 145 (FIGS. 16 and 20). A remarkable feature of this last embodiment is the fact that lamp 223 (FIG. 21) has only to be lighted up to replace at instant an acoustical intensity image by a phase image from the point of view of detectors 143, 169, 170 or others, with or without demodulation by system 145 (FIG. 20). Moreover, a lateral displacement 225 of hologram 220 by means of some screw, allows contrast inversion and continuous various of the aspect of the resulting phase image.

In all cases, the acoustical hologram formed in the liquid crystal layer of cell 120 can be rapidly erased by producing an alternating electric field to rapidly reorient the L.C. molecules, the way it has been described above in relation with FIG. 7. The alternating voltage supply 177 (FIG. 16) activated by control system 148 can be connected to conductive layers inside the L.C. cell, of which at least one is semi-transparent to light, as the one illustrated in FIG. 7. Or still the supply can be connected to reflective conductive layer 16 of FIGS. 7 and 8 to an external electrode 176 (FIGS. 8, 16) in the moderately conductive liquid which propagates the ultrasonic wave. In this case, the problem of light reflection by a semi-transparent electrode such as 15 in FIG. 7 is eliminated.

With the present invention, the image defects caused by coherence of ultrasonic waves irradiating the object can be largely corrected. It is a well known fact that coherence of these waves produce undesirable diffraction effects by structures in the object, out of the plane of interest. In some other acoustic imaging systems of the previous art, this problem is solved by using frequency sweeping of the ultrasonic transducers between fixed limits and superposing the images obtained at all frequencies. In the various embodiments of the present invention, these defects can be corrected by superposing the series of images obtained while varying the phase relationship between the various points of the object irradiated by a fixed frequency source. This phase variation is essentially produced by changing gradually the orientation of the transducer irradiating the object, as indicated in FIG. 16 by mechanism 175.

Transducer 127 for transmission imaging can rotate with two degrees of freedom about point 0 near the center of acoustic lenses system 121, and several image-holograms can successively be taken and demodulated by means of system 145 (FIGS. 16 and 20). The resulting images can then be superposed in video memory 192 or in any image processing system 193. These images can also be photographed in succession and superposed on film by means of a camera placed in front of video monitor 146. Transducer 127 is moved by motor 175 which can be mechanical, hydraulic, electrical or of any other type, and can rotate independently in the plane of the figure and in the perpendicular plane passing through point 0. FIG. 16 shows three possible positions of transducer 127 after having rotated in the plane of the figure. This rotation is typically less than 10° in both planes. For the same reasons, transducer 149 used in imaging by scattering can be rotated in a similar way about a point generally located on the other side of object 124. With transducer 149, the acquisition and superposition of successive images is done the same way.

Another way of obtaining a visible image from the acoustical of an object directly converted to a visible hologram by acousto-optical cell 120 (FIG. 16) is illustrated in FIG. 22. It is a purely optical technique where the previous (FIG. 16) incoherent light source is replaced by a laser 230, associated with lens 231 and spatial filter 232 to give a coherent beam of light incident on the optical system which is substantially the same as previously (FIG. 16). The emerging convergent beam of light is refracted into a cylindrical beam 235 by lens 139. This beam is diffracted by the hologram formed in the liquid crystal layer of cell 120. The reflected light is principally diffracted in spectra of order −1 (237), 0 (238) and +1 (239). By means of spatial filter 236, the two first orders are stopped. The remaining light energy comes out of the optical system as beam 240 converging towards an appropriate detector, such as a video camera 143, a photographic camera 170, the eye of an observer 169 or any other detector. This way, the visible image of an acoustical object is formed by direct optical conversion of an image-hologram given by liquid crystal cell 120. In this case, the resulting image is generally coincident with the plane of cell 120.

FIG. 23 shows another way of using a reflecting liquid crystal convertor in the case where it is not required to use hydro-acoustic lenses to form the acoustical image of an object. This method can be used in particular when it is desired to visualize the acoustic intensity distribution in front of a transducer, or to visualize the acoustical shadow of an object projected on the L.C. convertor. This system is simpler than the one of FIG. 16, but both have certain elements in common. Enclosure 179 is covered inside with a sound absorbing material 241 containing a liquid 125 for propagation of ultrasonic energy. The external optical system formed of lens 172, light source 132, condenser 133, detector 143 and sub-system 161' is essentially the same as the one described in relation with FIGS. 16 and 18. Subsystem 161' is essentially the same as 161 of FIG. 16, less the source and condenser. The liquid crystal cell 120 is substantially normal to axis XX' of the system. Transducer 128 generates plane ultrasonic waves in the direction of cell 120. Waves which are partially transmitted or reflected by 120 are absorbed by coating 241. Ultrasonic source 178 of which it is required to visualize the intensity pattern is generally located in front of cell 120 as illustrated. Both sources like 128, 178 can be placed on either side of L.C. cell 120 as required: It is another remarkable feature of the invention, in its various embodiments, as in FIGS. 16, 18, etc. In FIG. 23, plate 130 has the same functions as in FIG. 16. Like transducers 127, 128 of FIG. 16, transducers 128, 178 of FIG. 23 are connected to the same source of high frequency electrical energy and radiate coherent ultrasonic waves. These waves produce on cell 120 patterns of interference fringes which contrast is modulated by acoustic intensity distribution in front of transducer 178. In the case where it is required to visualize the shadow of an object irradiated by ultrasonic waves, this object is placed between transducer 178 giving plane uniform waves and the L.C. cell 120.

FIG. 24 shows an ultrasonic holographic camera incorporating a reflecting acousto-optical liquid crystal cell with essentially the same features than system previously described in FIG. 16, but where optical system 161 of FIG. 16 is replaced by system 300 which incorporates certain particular advantages. If we refer to FIG. 16, it is seen that light travelling both ways through lenses 138 and 139 is linearly polarized. Now, the angle between the plane of polarization and the plane of incidence of light varies from point to point on the lenses surfaces. It follows that transmitted light becomes more or less elliptically polarized according to the importance of reflections on the various interfaces. This light is therefore partially transmitted by polarizer or analyser 141, and it can be difficult to have a uniformly dark field from the point of view of a detector such as 143 when the L.C. in cell 120 is not distorted in its normal state. But this problem can be corrected if multiple reflections on lenses 138, 139 are radically reduced by means of multiple anti-reflection coatings. Optical system 300 of FIG. 24 does not have these requirements, has a smaller number of lenses needing only simple anti-reflection coatings if any, since linearly polarized light interacts only with flat surfaces. Point-like light source 301, white or sensibly monochromatic, is located in focal plane of lens 302, on axis Y'''Y''' or in its vicinity. This lens must be large enough, so as to produce a cylindrical light beam 160 covering the largest portion of cell 120 after reflection on beamsplitter 304. The beam is linearly polarized by polarizer 303 which axis of polarization is coincident with plane of incidence on 304, or perpendicular to this plane. The fraction of light passing through 304 is absorbed in a light trap 305 which is similar to 144 in FIG. 16. When the L.C. molecules in cell 120 are not distrubed, the L.C. being nematic and homotropic, the cylindrical light beam 160 is reflected through the L.C. layer with no modifications of its polarization state: reflected light is linearly polarized. Therefore, the reflected light beam can be strongly and uniformly stopped by polarizer or analyzer 306 appropriately oriented relative to polarizer 303. In this case, the field seen by detectors such as 143, 169, 170 or others, is uniformly dark. When the L.C. layer in 120 is distorted under the action of ultrasonic waves 116, 116', light reflected through the cell becomes elliptically polarized such that it is then partially transmitted through analyser 306 and detected by 143, etc. The detector then sees a light area on a dark background, corresponding to an area where acoustic energy is incident and distorts the L.C. structure in cell 120. Axis Y'''Y''' of optical system 300 is preferably inclined by 45° above the plane determined by ultrasonic beams 116 and 116', the same way as in the system shown in FIGS. 16, 17. It follows that the plane of polarization of light entering enclosure 117 through window 140 makes an angle substantially equal to 45° with the plane determined by acoustic beams 116 and 116' (the figure plane). Furthermore, axis X'X'' of optical system 300 is preferably at a small angle ϵ relative to axis XX', in such a way that light rays 308 reflected by entrance window 140 are deflected from the entrance pupil of detector 143, 169, 170, or any other. The center of this entrance pupil can be on axis X'X'' or in the vicinity of this axis. Lenses 302 and 307 may be, for example, aspheric lenses molded in plastic material, with preferably anti-reflection coatings. One particular feature of this embodiments and of all others incorporating the present acousto-optical liquid crystal cells is the capability to give at will positive or negative images, that is to represents visually an area on the cell where acoustic intensity is higher as a clear spot on a dark background, or as a dark spot on a clear background. This can be done in systems of FIGS. 16, 23, 24 by changing slightly the angle between X'X'' and Y'''Y''', the light source 301 and detector 143 being on the axes or near the axes. All the other elements in FIG. 24, other then those of the optical system 300, are essentially the same as those in FIGS. 16, 17 and 23, and have the same purpose as described above.

FIG. 25 shows another embodiment of acoustical imaging system incorporating a liquid crystal acousto-optical convertor with stratified rigid walls, or with polymeric membrane walls. This cell is optically transparent. A particular advantage of this embodiment resides with the ease of adjustment of the optical system for maximum sensitivity. The object to be examined 406 may be placed in compartment 402 filled with liquid 404 and separated from other compartment 401 by an acoustically transparent membrane 405. Object 406 is irradiated either by transducer 407 when a transmisson acoustic image of the object is required, or laterally by ultrasonic transducer 425 to have an image by scattered acoustic energy. Ultrasonic energy coming out of the object passes freely through 405 and is received by acoustic lens 410 after reflection by plane wall 409. Lens 410, as in systems of FIGS. 16, 24, are preferably made of strong polymeric film tensioned over rings bolted together and containing a liquid in which the velocity of sound is substantially lower than that in adjacent liquid 403, with volume that can be changed by means of a pump (not represented), allowing changes of the acoustic focal length for acoustical image focusing. Acoustic energy refracted by lens 410 is reflected by plate 411 which is optically transparent, and is focused on liquid crystal acousto-optical cell 400 where the acoustic field distribution represents acoustic intensity distribution in a transversal plane of object 406. This energy meets cell 400 at near normal incidence and easily goes through it with minimum multiple reflections, allowing maximum interaction with the liquid crystal layer in 400. The acoustic energy emerging from cell 400 is then reflected by optically transparent plate 412 and absorbed by coating 413 on the inside walls on enclosure 401. A second transducer is also placed in front of cell 400 at an angle of about 45°, so that the acoustic energy emitted by 414 is incident obliquely on 400, a large fraction passing freely through 400 and producing an interaction with the liquid crystal layer, the emerging energy being absorbed by coating 413. The reflected fraction of the energy is also absorbed by the part of coating 413 in front of cell 400. The two ultrasonic waves 408, 415 being substantially coherent, interfere in the plane of 400 to give the image-hologram of object 406, which image-hologram is made visible by means of the remarkable properties of the liquid crystal acousto-optical according to the present invention, that were previously described. Cell 400 is simultaneously crossed by a substantially cylindrical light beam 418 which polarisation plane makes an angle of about 45° with the plane determined by acoustic rays 408 and 415 (plane of the figure). This light comes from a small size source 416 of white light or substantially monochromatic light placed at the focus of converging lens 417 outside of enclosure 401. The cylindrical beam given by this lens is then polarized by polarizer 419 which polarization axis makes an angle of about 45° with the plane of the figure. The emerging light beam goes through optically transparent plate 411, L.C. cell 400, optically transparent plate 412 and is analyzed by polarizer 420. Lens 421 makes the emerging light energy to converge towards a suitable detector 422 that may be similar to those described in relation with FIGS. 16, 17, 23, 24. All the different ways to observe and process acoustical holograms and images in relation with systems of FIGS. 16, 17, 20, 21, 22, 23 and 24 are applicable to the system of FIG. 25.

I claim:

1. Apparatus for acoustic imaging of an object, comprising:

a main enclosure subdivided into a first and a second compartment, each containing a liquid medium allowing propagation of ultrasonic waves, the said compartments being separated by an acoustically transparent membrane;

a first large area ultrasonic transducer located in the first compartment;

a first system of hydro-acoustic lenses;

an acoustic-optical cell comprising an oriented liquid crystal layer, contained between stratified walls having an acoustic impedance matched to the acoustic impedance of the propagation media adjacent to said walls for widely varying values of incidence angles, in such a way that the ultrasonic waves incident on said cell pass freely through said cell with minimum reflections on said walls of said cell, so producing maximum interaction with said liquid crystal, the molecules of said liquid crystal being induced to reorient perpendicularly to the acoustic displacement, the initial orientation of said molecules being preferably perpendicular to said walls, at least one of said walls being optically transparent, a plate made of an optically transparent and acoustically reflecting material; and an optical exit window, all located inside the second compartment and disposed along the same principal axis passing through the acoustically transparent membrane;

an optical system to produce and send a light beam on the liquid crystal cell; and an acoustic absorber located inside the second compartment, but away from the principal axis, said absorber being placed so as to absorb the ultrasonic waves coming from the first compartment into which is placed the object to be visualized and being reflected by said acoustically reflecting plate which is for this purpose at an angle relative to the principal axis, the diopter or exit window being used to see the acoustic image, wherein is comprised a second large area ultrasonic transducer, laterally located away from the principal axis, between the first lens system and the said liquid crystal cell, the said second transducer being placed in such a way as to emit a plane acoustic wave toward the said cell, a fraction of this obliquely emitted wave passing through the cell and being absorbed by the acoustic absorber which also receives the waves coming the first compartment, another fraction of this obliquely emitted wave being reflected on said cell and also absorbed by the acoustic absorber which extends on both sides of said cell, said second transducer being excited by the same generator than the first transducer.

2. Apparatus as in claim 1 wherein there are means to move the transducer inside the first compartment along an arc of a circle with its center located near the object, on the principal axis of the apparatus.

3. Apparatus as in claim 2 wherein the said transducer can be located alternately in a position on the principal axis of the apparatus and in a position radially located relative to the said axis.

4. Apparatus as in claim 1 wherein there is a second enclosure including the system sending light on the cell, the said system emitting a light beam toward the main enclosure through the optical window, the said window being a first opening in the said second enclosure, and this last enclosure comprising a system to visualize the acoustic image through the said optical window and a second opening in the said second enclosure, the said lighting and visualization systems being optical.

5. An acousto-optical cell, comprising an oriented nematic liquid crystal layer contained between multi-layered walls, at least one of said walls being comprised of two rigid plates having substantially the same thickness, said plates being separated by a different material having a substantially lower acoustic impedance than the plates, said cell achieving good acoustic impedance matching with an adjacent propagation medium for widely varying angles of incidence of the acoustic energy.

6. Liquid crystal cell according to claim 5 wherein one of the layers in at least one of walls of the said cell is composed of an optical polarizing material.

7. Liquid crystal cell of claim 5 wherein an electrically conducting and optically reflecting or semi-reflecting film is interposed between two rigid layers of at least one of the said walls, in such a way as to reflect the light waves having passed through the said liquid crystal and to create in the said liquid crystal an alternating electric field to reorient the molecules of the said liquid crystal, when the said conductive layer is connected to one pole of an alternating voltage supply, the other pole being connected to another conductive film acting as an electrode on the opposite side of the said liquid crystal layer, inside the other wall of the said cell.

8. Liquid crystal cell of claim 5 wherein an electrically conducting and at least optically semi-reflecting film is interposed between two rigid layers of at least one of said walls, in such a way as to reflect the light waves having passed through said liquid crystal and to create in said liquid crystal an alternating electric field to reorient the molecules of said liquid crystal when said conductive layer is connected to one pole of an alternating voltage supply, the other pole being connected to another conductive film acting as an electrode on the opposite side of said liquid crystal layer outside and nearby in said propagation medium of ultrasonic waves.

9. An acousto-optical cell of claim 5, 7, or 8 wherein the liquid crystal is a nematic compound of positive dielectric anisotropy.

10. An acousto-optical cell, comprising an oriented nematic liquid crystal layer contained betwen multilayered walls, at least one of said walls being comprised of three rigid plates separated by a different material having a substantially lower acoustic impedance than the plates, two of said plates being external to the third one which is intermediate, said two plates having substantially half the thickness of the third one, said cell achieving good acoustic impedance matching with an adjacent propagation medium for widely varying angles of incidence of the acoustic energy.

11. An acousto-optical cell of Claim 5 or 10 wherein said plates are made of thin glass.

12. An acousto-optical cell of Claim 5 or 10 wherein the material between the plates is a polymerized resin.

* * * * *